United States Patent
Anderson et al.

(10) Patent No.: US 8,466,147 B2
(45) Date of Patent: Jun. 18, 2013

(54) USE OF REVERSINE AND ANALOGS FOR TREATMENT OF CANCER

(75) Inventors: Kenneth C. Anderson, Wellesley, MA (US); Nicholas Mitsiades, Roxbury, MA (US); Joseph Negri, Jamaica Plain, MA (US); Douglas W. McMillin, Cambridge, MA (US); Constantine S. Mitsiades, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 642 days.

(21) Appl. No.: 12/514,360

(22) PCT Filed: Nov. 12, 2007

(86) PCT No.: PCT/US2007/023839
§ 371 (c)(1),
(2), (4) Date: Mar. 12, 2010

(87) PCT Pub. No.: WO2008/060535
PCT Pub. Date: May 22, 2008

(65) Prior Publication Data
US 2010/0172893 A1 Jul. 8, 2010

Related U.S. Application Data

(60) Provisional application No. 60/865,271, filed on Nov. 10, 2006.

(51) Int. Cl.
*A61K 31/52* (2006.01)
(52) U.S. Cl.
USPC ...................................................... 514/234.2
(58) Field of Classification Search
None
See application file for complete search history.

(56) References Cited

U.S. PATENT DOCUMENTS

| | | |
|---|---|---|
| 6,492,333 B1 | 12/2002 | Mundy |
| 6,884,804 B2 | 4/2005 | Choon-Moon |
| 6,986,891 B2 | 1/2006 | Gelber |
| 6,992,207 B2 | 1/2006 | Lewensohn et al. |
| 7,094,885 B2 | 8/2006 | Fritzberg |

FOREIGN PATENT DOCUMENTS
WO  WO-2005/047524 A2  5/2005

OTHER PUBLICATIONS

Zhu et al. Blood, 2005, vol. 105, pp. 4759-4766; Published Online Feb. 22, 2005.*
Wisloff et al. European Journal of Haematology, 1992, vol. 48, No. 2, pp. 70-74 (Abstract attached).*
Roos et al. Leukemia Research, 1987, vol. 11, No. 6, pp. 519-524.*
Mujagic et al. Cancer Research, 1983, vol. 43, pp. 3591-3597.*
Anastasia et al., "Reversine-Treated Fibroblasts Acquire Myogenic Competence in vitro and in Regenerating Skeletal Muscle," *Cell Death and Differentiation*, 13:2042-2051 (2006).
Chen et al., "Dedifferentiation of Lineage-Committed Cells by a Small Molecule," *J. Am. Chem. Soc.*, 126(2):410-411 (2004).
Gey, C. and Giannis, A., "Small Molecules, Big Plans—Can Low-Molecular-Weight Compounds Control Human Regeneration?," *Angew. Chem. Int. Ed. Engl*, 43(31):3998-4000 (2004).
Hines, J., "Small Molecules Driving Myotube Fission," *Chem. Biol.*, 12(10):1058-60 (2005).
Hsieh et al., "Effects of 2,6-Disubstituted Purine Reversine on Growth and Cell Cycle Control in Hormone Refractory Prostate Cancer PC-3 Cells", *FASEB Journal*, 20(4):A37-A38 (Part 1) (2006).
McMillin et al., "Reversine: A Chemical Probe Providing Insight into Myeloma Biology and Potential Therapeutic Applications," *Blood*, 108(11):992A-993A (Part 1) (2006).
Wisloff et al., "Bolus Therapy with Mitoxantrone and Vincristine in Combination with High-Dose Prednisone NOP-Bolus in Resistant Multiple Myeloma," *European Journal of Hematology*, 48(2):70-74 (1992).

* cited by examiner

*Primary Examiner* — James D Anderson
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

Herein is provided methods and compositions for treating cancer. In one embodiment, a method is provided for treating a patient suffering from cancer, the method comprising administering to the patient an effective amount of reversine, reversine analog or reversine containing agent. In another embodiment, compositions comprising reversine are provided. Such compositions may further comprise additional active agents and other additives. The compositions and methods provided herein are useful, for example, in the area of medicine.

28 Claims, 19 Drawing Sheets

PBMCs= peripheral blood mononuclear cells
PHA=phytohaemagglutinin

| Name | Tissue type | EC50 (µM) |
|---|---|---|
| KM101 | stromal cell line | 1.8 |
| KM103 | stromal cell line | 5.7 |
| KM104 | stromal cell line | 4.8 |
| KM105 | stromal cell line | 5.9 |
| HS-5 | stromal cell line | 4.2 |
| Normal stroma | normal donor stroma | 3.8 |
| THLE-3 | immortalized hepatocyte cell line | >10 |

USE OF REVERSINE AND ANALOGS FOR TREATMENT OF CANCER

RELATED APPLICATIONS

This application is a national stage application, filed under 35 U.S.C. §371, of International Application No. PCT/US2007/023839, filed on Nov. 12, 2007, which claims the benefit of and priority to U.S. Ser. No. 60/865,271, filed on Nov. 10, 2006, each of which is herein incorporated by reference in its entirety.

TECHNICAL FIELD

This disclosure relates generally to compositions and methods useful in the treatment of disease. In particular, the compositions and methods disclosed herein are useful in treating cancer and conditions associated with cancer. The disclosure finds utility, for example, in the fields of medicine and medicinal chemistry.

BACKGROUND

Chemotherapeutic methods, often in combination with alternative forms of treatment such as radiation therapy, provide the best hope for treatment of many forms of cancer and other conditions of unwanted cellular growth. Cancers that comprise solid tumors, either malignant or benign, are often treated with chemotherapeutic methods. This is also true for conditions that are not well-suited for treatment by surgical methods, such as malignant cancers and cancers that are not characterized by the formation and growth of tumors. Conditions classified as hematological malignancies are commonly treated using chemotherapeutic methods. Specific types of hematological malignancies include leukemia, lymphoma, and multiple myeloma. Specific types of solid tumors include thyroid cancer, breast cancer, prostate cancer, and others. Unfortunately, cures are not yet available for many cases of hematological malignancies and solid tumors; treatment often focuses instead on containment of the disease and improvement of the patient's quality of life.

For example, multiple myeloma (MM) embodies a plasma cell disorder characterized by clonal neoplastic proliferation of plasma cells engaged in the production of a monoclonal immunoglobulin, usually monoclonal IgG or IgA. MM accounts for 1% of all malignant disease and slightly more than 10% of all hematologic malignancies, with over 15,000 new cases of the disease diagnosed in the United States in 2005.

A variety of methods have been developed for treating myeloma. For example, U.S. Pat. No. 7,094,885 describes a method of treating conditions that arise in or near bone such as myeloma, with compositions having as their active ingredient a radionuclide complexed with a chelating agent such as macrocyclic aminophosphonic acid.

U.S. Pat. No. 6,992,207 describes alkylating di- and tripeptides based on a melphalan unit, and one or two additional amino acids or amino acid derivatives, which can be used in the treatment of carcinogenic diseases such as myeloma.

U.S. Pat. No. 6,986,891 describes a method of killing or inhibiting the growth of myeloma tumor cells or ovarian cancer tumor cells comprising administering to an individual in need thereof a composition comprising a monoclonal antibody.

U.S. Pat. No. 6,884,804 describes compounds that are inhibitors of protein kinase, particularly inhibitors of Src mammalian protein kinase involved in cell proliferation, cell death and response to extracellular stimuli. Pharmaceutical compositions comprising the inhibitors are used in the treatment and prevention of various disorders including myeloma.

U.S. Pat. No. 6,492,333 describes the identification and use of compositions for treating myeloma bone disease. The compositions inhibit proteasomal activity and decrease the activity of the transcription factor NF-kB. Assessment of a candidate compound for its ability to inhibit production or activity of proteasomal enzymes or NF-kB is explored as a means to identify agents to treat myeloma bone disease.

Therapy for MM includes induction, maintenance, and supportive aspects. The induction portion of the treatment aims at reducing the volume of diseased plasma cells and achieving a plateau phase. Different drugs and treatment modalities, including bone marrow transplantation, are under investigation, and MM remains a subject of research in the medical profession. Nevertheless, most patients having MM succumb to the disease within 36-48 months from the time of diagnosis. The limitations of effective therapy for MM are primarily associated with a low cell proliferation rate and multi-drug resistance.

An ideal chemotherapy-based method of treatment of cancers such as hematological malignancies would be effective on a variety of tumor cell lines. An ideal chemotherapeutic agent for such methods would be readily available and/or easily prepared, and would not interfere with (or, better still, would be synergistic with) other chemotherapeutic treatments that may be administered concurrently. The ideal chemotherapeutic candidate compound would effectively treat tumor cells at concentrations that are not toxic to healthy cells. In addition, the ideal method of treatment would effectively treat tumor cells with minimal administrations of the active agent(s). Using these ideal characteristics as a guide, the present disclosure provides compositions and methods of treatment of cancer that are directed at addressing one or more of the abovementioned limitations, as well as related issues in the fields of medicine and medicinal chemistry.

SUMMARY OF THE INVENTION

The present disclosure describes compositions and methods comprising reversine for treating cancer.

In one embodiment, then, is provided a method for treating cancer in a patient. The method comprises administering to the patient a therapeutically effective amount of reversine or a pharmaceutically acceptable salt thereof.

In another embodiment is provided a method for treating cancer in a patient comprising administering to the patient a therapeutically effective amount of an anti-cancer agent. The anti-cancer agent does not substantially suppress NF-kB activity.

In yet another embodiment is provided a method for killing or inhibiting the growth of cancer cells comprising administering to a patient in need thereof an effective amount of reversine or a pharmaceutically acceptable salt thereof.

In a further embodiment is provided a method for increasing the susceptibility of myeloma cells in a patient to a tumoricidal agent by slowing or arresting the cell cycle of the myeloma cells. The method comprising administering to the patient an effective amount of reversine.

In a still further embodiment is provided a method for treating cancer in a patient in need thereof The method comprises administering to the patient a composition comprising: (a) a first compound capable of slowing or arresting the cell cycle of myeloma cells in the G2 phase of the cell cycle; and (b) a tumoricidal agent.

In a still further embodiment is provided a pharmaceutical composition for treating cancer in a patient. The composition comprises reversine or a pharmaceutically acceptable salt thereof and a pharmaceutically acceptable carrier.

DETAILED DESCRIPTION OF THE INVENTION

Definitions and Nomenclature

Figure 1:
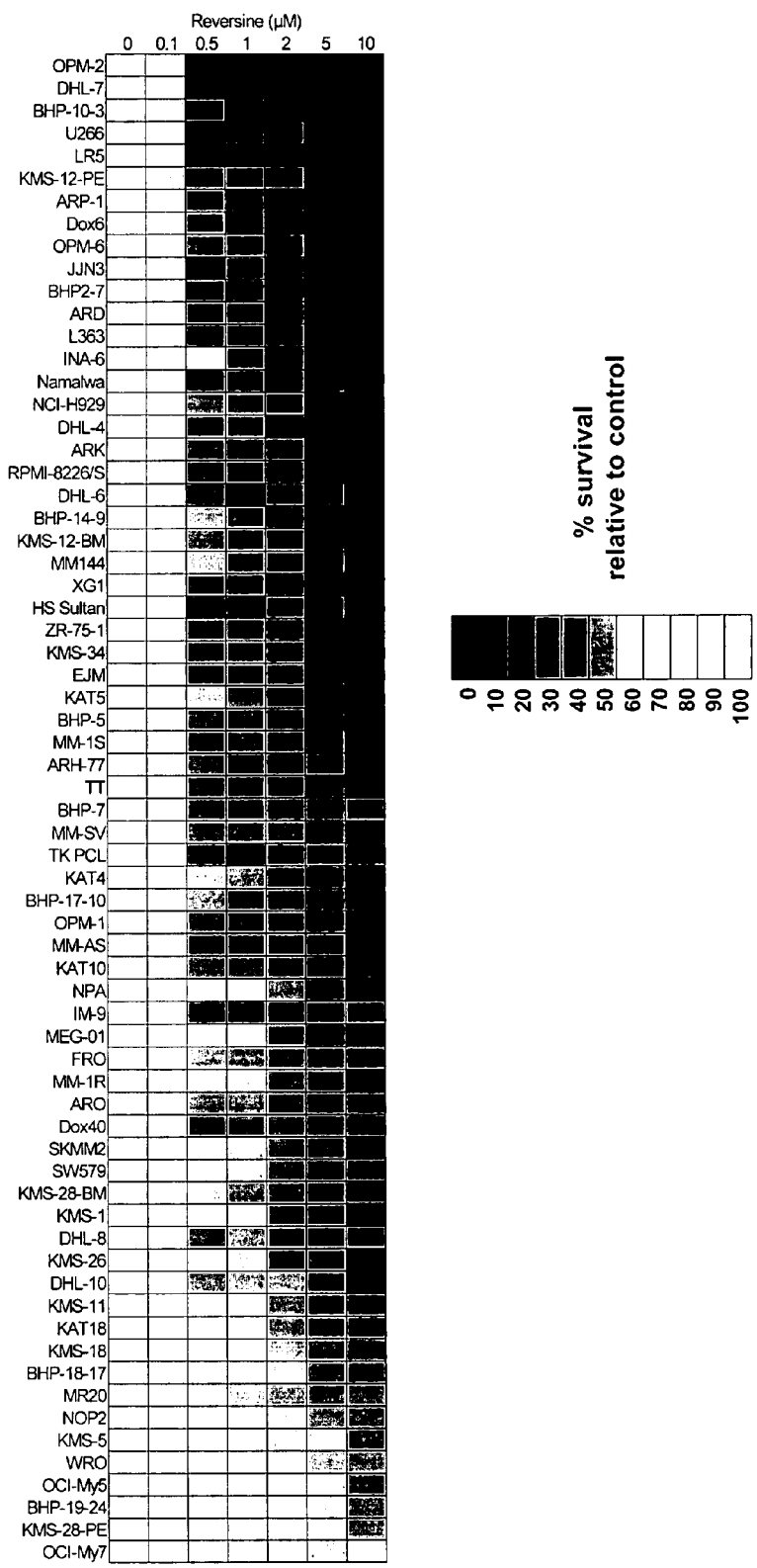
FIG. 1, described in Example 1, is a chart showing anti-cancer effects of reversine on a variety of tumor cell lines.

Before describing the present invention in detail, it is to be understood that unless otherwise indicated, this invention is not limited to particular dosages, formulations or methods of use, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a dosage form" refers not only to a single dosage form but also to a combination of two or more different dosage forms, "an active agent" refers to a combination of active agents as well as to a single active agent, and the like.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

When referring to a compound of the invention, applicants intend the term "compound" to encompass not only the specified molecular entity but also its pharmaceutically acceptable, pharmacologically active analogs, including, but not limited to, salts, polymorphs, esters, amides, prodrugs, adducts, conjugates, active metabolites, and the like. When the term "compound" is used, then, it is to be understood that applicants intend to include that compound per se as well as pharmaceutically acceptable, pharmacologically active salts, polymorphs, esters, amides, prodrugs, adducts, conjugates, metabolites, and other such derivatives, analogs and related compounds.

The terms "treating" and "treatment" as used herein refer to reduction in severity and/or frequency of symptoms, elimination of symptoms and/or underlying cause, prevention of the occurrence of symptoms and/or their underlying cause (e.g., prophylactic therapy), and improvement or remediation of damage.

By the terms "effective amount" and "therapeutically effective amount" of a compound of the invention is meant a nontoxic but sufficient amount of the drug or agent to provide the desired effect.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

By "patient" is meant any animal for which treatment is desirable. Patients may be mammals, and typically, as used herein, a patient is a human individual.

Compositions

"Reversine" is the common name for the unnatural purine derivative 2-(4-morpholinoanilino)-6-cyclohexylaminopurine. Reversine has attracted attention for its ability to trigger myoblasts to dedifferentiate into multipotent progenitor-type cells. The multipotent progenitor cells are capable of differentiating into either adipocytes or osteoblasts (Hines, J. Chem. Biol. 2005, 12(10):1058-60; Gey, C. and Giannis, A. Angew. Chem. Int. Ed. Engl. 2004, 43(31):3998-4000; Chen et al. J. Am. Chem. Soc. 2004 126(2):410-411). In another study, primary murine and human fibroblasts treated with reversine were induced to differentiate into skeletal muscle (Anastasia et al., Cell Death and Differentiation, 26 May 2006, advanced online publication). Because of this activity, it was hypothesized that reversine might be capable of causing dedifferentiation in myeloma cells, thereby allowing the preparation of myeloma stem cells from mature cells. However, rather than causing myeloma cells or other tumor cells to dedifferentiate, reversine causes tumor cell death as described herein.

Accordingly, in one embodiment, the compositions described herein comprise reversine. Furthermore, in one embodiment, the methods described herein comprise the administration of reversine to a patient in need thereof.

The compositions of the current disclosure comprise, as an active agent, reversine in a pharmaceutically acceptable form. If desired, the compositions may further comprise one or more additional active agents, as described in detail below. The active agents, including reversine, may be administered in the form of the compound per se, as well as in the form of a salt, polymorph, ester, amide, prodrug, derivative, or the like, provided the salt, polymorph, ester, amide, prodrug or derivative is suitable pharmacologically. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically pure form.

The one or more additional active agents, when present, may be selected from any biologically active agent, provided that the additional active agent is reversine-compatible. By "reversine-compatible" is meant that the additional active agent does not undesirably react with or otherwise interfere with the pharmaceutical activity and availability of reversine. Such active agents may be recognized using established methods for testing pharmaceutical formulations.

The active agent suitable for the compositions and methods disclosed herein may be any known or hereafter discovered pharmacologically active agent, and may be a compound that occurs in nature, a chemically modified naturally occurring compound, or a compound that is chemically synthesized. Active agents include any compounds, compositions, molecules, elements, ions, biomolecules, or fragments thereof that may be administered to a patient. Classes and examples of active agents include: amino acids; analgesic agents; anesthetic agents; anti-Acquired Immunodeficiency Syndrome (AIDS) drugs; anti-arrhythmic agents; anti-arthritic agents; antibiotics; antibodies; anti-cancer drugs including anti-neoplastic drugs; anti-cholinergics; anti-coagulative agents; anti-convulsants; anti-depressants; anti-diabetic agents; anti-diarrheals; anti-helminthics; anti-histamines; anti-hyperlipidemic agents; anti-hypertensive agents; anti-infective drugs; anti-inflammatory drugs; anti-migraine preparations; anti-nauseants; anti-Parkinson drugs; anti-proliferative agents; anti-pruritics; anti-psychotics; antipyretics; anti-spasmodics; anti-tubercular agents; anti-ulcer agents; anti-viral agents; anxiolytics; appetite suppressants; attention deficit disorder (ADD) and attention deficit hyperactivity disorder (ADHD) drugs; beta-blockers; biopharmaceuticals; cardiovascular preparations including calcium channel blockers; CNS agents including CNS stimulants; complexing agents; cough and cold preparations including decongestants; cytokines; cytotoxic agents; diuretics; drugs including analogs and derivatives and their metabolic products; drugs of abuse; genetic materials; growth factors; herbal remedies; hormones including thyroid hormones; hormonolytics; lipids; hypnotics; hypoglycemic agents; immunomodulators; immunosuppressive agents; leukotriene inhibitors; metabolites; minerals; mitotic inhibitors; muscle relaxants; narcotic antagonists; neuro-modulators; neurotropic drugs; nicotine; nucleotides; nutritional agents including essential amino acids, fatty acids, and nutrients; ophthalmic drugs such as anti-glaucoma agents; parasympatholytics; pharmaceuticals; pro-coagulative agents; psychotropic medications; psychostimulants; radical quenchers; respiratory drugs including anti-asthmatic agents; saccharides; sedatives; steroids; sympathomimetics; tranquilizers; triglycerides; tumoricidal agents; vaccines; vasodilators including general coronary, peripheral and cerebral vasodilators; vitamins; and combinations and/or derivatives thereof.

Further examples of active agents suitable for the drug delivery systems and methods disclosed herein also include macromolecular active agents. Typically, macromolecular active agents have a molecular weight greater than 300 Da. Macromolecular active agents include biomolecules such as DNA, RNA, antisense oligonucleotides, peptidyl drugs (i.e., peptides, polypeptides and proteins, including fluorescent proteins), ribosomes and enzyme cofactors such as biotin, oligonucleotides, proteins, peptides, enzymes, plasmids, prions, and polysaccharides.

Specific examples of additional active agents include, without limitation, agents selected from acaricides, actinomycin-D, aldesleukin, aminoglutethimide, amsacrine, anastozole, angiostatin, L-asparaginase, avermectins, azalides, 5-azacytidine, aziridinylbenzoquinone, bafilamycin, bioallenthirn, bleomycin, bicalutamide, bortezomib, bredinin, bryostatin 1, buserelin, busulfan, carboplatin, carmustine, chivosazol A, chlorambucil, cisplatin, cladribine, colchicine-fosfamide, copiamycin, cyclophosphamide, cyproterone, cytarabine, dacarbazine, dactinomycin, daunorubicin, deoxycoformycin, desertomycin, difficidin, diethylstilbestrol, docetaxel, dorametin, doxorubicin, doxycycline, endostatin, epirubicin, eprinmectin, estramustine, etoposide, fludarabine, fludrocortisone, 5-fluorodeoxyuridine, 5-fluorouracil, fluoxymesterone, flutamide, geldanamycin, gemcitabine, genistein, grahamimycins, goserelin, hydroxyurea, idarubicin, ifosfamide, ilimaquinone, .alpha.-interferon, irinotecan, ivermectin, leucovorin, leuprolide, levamisole, lincomycin, lomustine, mathemycin, mechlorethamine, medroxyprogesterone, megestrol, megovalicins, melphalan, mercaptopurine, mesna, methotrexate, minocycline, mithramycin, mitomycin, mitotane, mitoxantrone, moxidectin, nilutamide, nocodazole, okadaic acid, octreotide, oocydin A, oxydifficidin, paclitaxel, pentostatin, plicamycin, porfimer, procarbazine, radicicol, rapamycin, retinoic acid, rhizoxin, sirolimus, staurosporine, streptozocin, sporaviridin, streptogramin, suramin, tamoxifen, tautomycin, teniposide, testolactone, 6-thioguanine, thiotepa, tolytoxin, topotecan, tryphostins, vinblastine, vincristine, vindesine, vinorelbine, virginiamycin, wortmannin, derivatives thereof, and combinations of any of the foregoing.

Additional examples of active agents suitable for administration in combination with reversine are tumoricidal agents including mitotic inhibitors such as vinca alkaloid derivatives such as vinblastine, vinorelbine, vindescine and vincristine; colchicines and colchicine derivatives including allocolchicine, and N-benzoyltrimethyl-methyl ether colchicinic acid; halichondrin; dolastatin 10; maystansine; taxanes; 2'-N-[3-(dimethylamino)propyl]glutaramate (taxol derivative); thiocholchicin; trityl cysteine; azathioprine; cytocine arabinoside; 2'2'-difluorodeoxycytidine (gemcitabine); adriamycin and mitamycin. Other examples include alkylating agents; carboplatin; oxiplatin; iproplatin; ethyl ester of N-acetyl-DL-sarcosyl-L-leucine (Asaley or Asalex); 1,4-cyclohexadiene-1,4-dicarbamic acid; 2,5-bis(1-azirdinyl)-3,6-dioxodiethyl ester (diaziquone); 1,4-bis(methanesulfonyloxy)butane (leucosulfan); chlorozotocin; clomesone; cyanomorpholinodoxorubicin; cyclodisone; dianhydroglactitol; fluorodopan; hepsulfam; mitomycin C; hycantheonemitomycin C; mitozolamide; 1-(2-chloroethyl)-4-(3-chloropropyl)-piperazine dihydrochloride; piperazinedione; pipobroman; porfiromycin; spirohydantoin mustard; teroxirone; tetraplatin; triethylenemelamine; uracil nitrogen mustard; bis(3-mesyloxypropyl)amine hydrochloride; nitrosourea agents such as cyclohexyl-chloroethylnitrosourea; methylcyclohexyl-chloroethylnitrosourea; 1-(2-chloroethyl)-3-(2,6-dioxo-3-piperidyl)-1-nitrosourea; bis(2-chloroethyl)nitrosourea; nitrogen mustard-related compounds; estramustine sodium phosphate; streptozocin; temozolamide; DNA anti-metabolites; cytosine arabinoside; hydroxyurea; 2-[(3hydroxy-2-pyrinodinyl)methylene]-hydrazinecarbothioamide; deoxyfluorouridine; 5-hydroxy-2-formylpyridine thiosemicarbazone; alpha-2'-deoxy-6-thioguanosine; aphidicolin glycinate; 5-azadeoxycytidine; beta-thioguanine deoxyriboside; cyclocytidine; guanazole; inosine glycodialdehyde; macbecin II; pyrazolimidazole; 2-chlorodeoxyadenosine; inhibitors of thymidylate synthase such as raltitrexed and pemetrexed disodium; clofarabine; floxuridine; DNA/RNA antimetabolites such as L-alanosine; acivicin; aminopterin and derivatives thereof such as N-[2-chloro-5-[[(2,4-diamino-5-methyl-6-quinazolinyl)methyl]amino]benzoyl]-L-aspartic acid, N-[4-[[(2,4-diamino-5-ethyl-6-quinazolinyl)methyl]amino] benzoyl]-L-aspartic acid, N-[2-chloro-4-[[(2,4-diaminopteridinyl)methyl]amino]benzoyl]-L-aspartic acid; soluble Baker's antifol; dichloroallyl lawsone; brequinar; dihydro-5-azacytidine; methotrexate; N-(phosphonoacetyl)-L-aspartic acid tetrasodium salt; pyrazofuran; trimetrexate; actinomycin D; cryptophycin and analogs such as cryptophycin-52 or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; tumor necrosis factor or the like; lectin inflammatory response promoters (selecting), such as L-selectin, E-selectin, P-selectin or the like; proteins, for example interferon; interleukins such as IL-2; and anti-hormones, for example anti-estrogens; anti-androgens such as Casodex™ (4'-cyano-3-(4-fluorophenylsulphonyl)-2-hydroxy-2-methyl-3'-(trifluoromethyl)propionanilide), and like molecules.

Carriers

Pharmaceutical compositions comprising reversine suitable for the uses described herein may also comprise a pharmaceutically acceptable carrier. Appropriate pharmaceutical carriers will depend, for example, on the method of administration.

Pharmaceutically acceptable carriers are materials such as binders, lubricants, disintegrants, fillers, surfactants, emulsifiers, coloring agents, and the like. Binders are used to impart cohesive qualities, and thus ensure that the composition remains intact (e.g., as an implant). Suitable binder materials include, but are not limited to, polymer matrices, hydrogels, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate manufacture, promoting powder flow and preventing particle capping (i.e., particle breakage) when pressure is relieved. Useful lubricants are magnesium stearate, calcium stearate, and stearic acid. Disintegrants are used to facilitate disintegration of the composition, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Surfactants are wetting agents, and may include ionic materials such as fatty acid salts and non-ionic materials such as PLURONICS™ (such as F-127, L-122, L-101, L-92, L-81, and L-61).

For example, the pharmaceutically acceptable carrier for the compositions disclosed herein may comprise one or more biocompatible polymer. By "biocompatible" is meant a material that does not illicit an adverse response when subjected to a biological environment such as by implantation or injection in vivo. Furthermore, in one embodiment, biocompatible materials do not illicit an immune response when administered in vivo. Unless otherwise stated, biocompatible materials include materials that are bioerodible, biodegradable and bioresorbable.

Polymer carriers such as biocompatible polymers may be homopolymers or copolymers of any of the monomer units described hereinbelow. Furthermore, copolymers are not limited to any specific architecture, and may consist of random, alternating, block (including multiblock), star, comb, graft, and dendrimer-type copolymers, as well as combinations thereof.

Blends of more than one bioerodible polymer are also within the scope of this disclosure. It will be appreciated that crosslinked and crosslinkable polymers may be used as long as such crosslinking does not adversely affect the material's ability to form the compositions described herein (e.g., the material's ability to bioerode). For example, reversible crosslinks (wherein the crosslinks comprise non-covalent and/or weakly covalent intermolecular bonds) may be present prior to administration of the compositions, or such bonds may form in vivo.

Suitable bioerodible polymers may comprise poly(orthoester)s, poly(lactone)s such as poly(epsilon-caprolactone) and poly(epsilon-caprolactone), poly(lactide)s, poly(lactic acid), poly(glycolide)s, poly(glycolic acid), poly(ethylene terephthalate), poly(butyric acid), poly(valeric acid), polymers of anhydrides, poly(vinyl alcohol), poly(ethylene vinyl acetate), polymers of alpha-hydroxycarboxylic acid and derivatives thereof, albumin, collagen, gelatin, hyaluronic acid, starch, cellulose and cellulose derivatives (e.g., methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(ether ester) multiblock copolymers, poly(ether)s such as poly(ethylene glycol), and poly(butylene terephthalate), tyrosine-derived polycarbonates, poly(hydroxyl acids), poly(hydroxybutyrate), polydioxanone, poly(alkylcarbonate), poly(hydroxyvaleric acid), polydioxanone, degradable polyesters, poly(malic acid), poly(tartronic acid), poly(acrylamides), polyphosphazenes, poly(amino acids), poly(alkylene oxide)-poly(ester) block copolymers, poly(hydroxybutyric acid), poly(beta-butyrolactone), poly(gamma-butyrolactone), poly(gamma-valerolactone), poly(d-decanolactone), poly(trimethylene carbonate), poly(1,4-dioxane-2-one) or poly(1,5-dioxepan-2-one), or combinations thereof (i.e., copolymers of the constituent monomer units, blends, etc.).

Examples of biodegradable polymers include synthetic polymers such as polymers of lactic acid and glycolic acid, polyanhydrides, poly(ortho)esters, polyurethanes, poly(butyric acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof In general, these materials degrade either by enzymatic hydrolysis or exposure to water in vivo, by surface or bulk erosion The components of a composition may be distributed homogeneously throughout the pharmaceutically acceptable carrier, or localized regions of concentration gradients may exist. By "homogeneous" distribution is meant to include instances of molecular homogeneity as well as bulk or macroscopic homogeneity. For example, for a composition comprising reversine in a carrier, the reversine may be homogeneously distributed on a molecular level (as for a solute homogeneously distributed within a solvent) or on a macroscopic level (as for discrete reversine particles homogeneously distributed throughout the carrier). Components of a composition may be covalently or otherwise attached to the pharmaceutically acceptable carrier.

For compositions administered as aqueous or other solvent-based dosage forms (e.g., for parenteral administration), a variety of liquid carriers may be used. Aqueous solutions may include salts, buffers, and the like. Non aqueous liquid carriers include, for example, fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like.

Additional Components

In addition to one or more pharmaceutically acceptable carrier, pharmaceutical compositions comprising reversine suitable for the uses described herein may also comprise one or more additional components. Additional components include, for example, salts, buffers, penetration enhancers, absorption accelerants, gel forming materials such as polymers, visualization aids, dispersing agents, stabilizers, excipients, and plasticizers.

Salts are compounds that ionize in aqueous solutions and may be employed, for example, to adjust the tonicity of the solution. If the active agent is present in the form of a salt, additional salts may be added to the composition in order, for example, to effect ion exchange with the active agent. Salts suitable for use with the compositions described herein are known in the art and include, for example, lithium, sodium, potassium, calcium, and magnesium salts having appropriate counterions that may be selected from chloride, bromide, iodide, carbonate, phosphate, nitrate, silicate, sulfate, phosphite, nitrite, sulfite, and the like.

Buffers are compounds or solutions that are employed to aid in maintaining the concentration of an analyte within a desired range. For example, pharmaceutically acceptable pH buffers are used to maintain the acidity or basicity of a solution within a pharmaceutically acceptable range. Buffers for use in the compositions disclosed herein may be any known or hereafter discovered buffer. Penetration enhancers include compounds that enable or enhance permeation of compositions across boundaries such as membranes. Examples of penetration enhancers may be found in the relevant literature (e.g., Percutaneous Penetration Enhancers, Smith and Maibach, eds., CRC Press, New York N.Y., 2005) and include cyclohexanone derivatives, cyclic monoterpenes, pyrrolidones, dioxolanes, 1-dodecylazacycloheptan-2-one (Azone), dimethylsulfoxide (DMSO), and limonene. Gel forming materials may be polymers or non-polymers, and are generally able to form a gelatinous network. In one embodiment, gel forming materials are able to form gels in vivo, whereas in other embodiments, gel formation takes place ex vivo. Examples of gel forming materials include collagen, chitosan, pectins, hyaluronic acid, and the like. Dispersing agents are surfactants (for example, as described herein) in combination with a solvent such as water. Plasticizers are compounds used to plasticize (i.e., soften) plastic and other materials. Examples include propylene glycol, acetyl tributyl citrate, acetyl triethyl citrate, p-tert-butylphenyl salicylate, butyl stearate, butylphthalyl butyl glycolate, dibutyl sebacate, di-(2-ethylhexyl) phthalate, diethyl phthalate, diisobutyl adipate, diisooctyl phthalate, diphenyl-2-ethylhexyl phosphate, epoxidized soybean oil, ethylphthalyl ethyl glycolate, glycerol monooleate, monoisopropyl citrate, mono, di-, and tristearyl citrate, triacetin (glycerol triacetate), triethyl citrate, and 3-(2-Xenolyl)-1,2-epoxypropane.

Excipients are inactive ingredients that may be employed in the compositions described herein for a variety of reasons. A wide range of excipients are described in the literature (e.g., Rowe et al., Handbook of Pharmaceutical Excipients, McGraw Hill, 2006).

Visualization aids are compounds that aid visualization of the drug delivery composition or any of the components thereof via a visualization method such as fluoroscopy, magnetic resonance imaging (MRI), visible light, ultrasound, or radiography. Visualization aids include biocompatible (non-toxic) radio-opaque materials, magnetic resonance imaging (MRI) responsive materials (i.e., MRI contrast agents), contrast agents, colorants, fluorescent materials, or echogenic materials. Examples of contrast agents include metrizamide, iopamidol, iothalamate sodium, iodomide sodium, meglumine, tantalum, tantalum oxide and barium sulfate, gold, tungsten and platinum powders, tungsten, barium carbonate, bismuth oxide, barium sulfate, metrazimide, iopamidol, iohexol, iopromide, iobitridol, iomeprol, iopentol, ioversol, ioxilan, iodixanol, iotrolan, acetrizoic acid derivatives, diatrizoic acid derivatives, iothalamic acid derivatives, ioxithalamic acid derivatives, metrizoic acid derivatives, iodamide, lypophylic agents, iodipamide and ioglycamic acid. MRI contrast agents (e.g., gadolinium (III) chelates or iron oxide compounds) may be incorporated into the composition. Visualization agents that can be included for characterization by visible light include dyes, pigments, and other colored agents. Coloring agents may be, for example, an endogenous compound (e.g., an amino acid or vitamin) or a nutrient or food material and may be a hydrophobic or a hydrophilic compound. Representative examples of colored nutrients (under visible light) include fat soluble vitamins such as Vitamin A; water soluble vitamins such as Vitamin B12 and folic acid; carotenoids such as β-carotene and lycopene, anthrocyanin and saffron extract, grape skin extract, beet red powder, beta carotene, annato, carmine, turmeric, paprika, α-tocopherolquinol (a Vitamin E derivative), L-tryptophan and so forth. Derivatives, analogs, and isomers of any of the above compounds may also be used.

In one aspect, the compositions of the present disclosure include one or more preservatives or bacteriostatic agents, present in an effective amount to preserve the composition and/or inhibit bacterial growth in the composition. Examples include bismuth tribromophenate, methyl hydroxybenzoate, bacitracin, ethyl hydroxybenzoate, propyl hydroxybenzoate, erythromycin, 5-fluorouracil, methotrexate, doxorubicin, mitoxantrone, rifamycin, chlorocresol, benzalkonium chlorides, paraoxybenzoic acid esters, chlorobutanol, benzylalcohol, phenethyl alcohol, dehydroacetic acid, sorbic acid, and the like.

Stabilizers include compounds such as antioxidants, and are used to inhibit or retard decomposition reactions that include, by way of example, oxidative reactions. Examples of stabilizer include butylated hydroxytoluene (BHT), butylated hydroxyanisole (BHA), ascorbic acid, ethylene diamine tetraacetic acid (EDTA), tocopherol-derived compounds such as alpha-tocopherol, sulfites, tert-butylhydroquinone, citric acid, acetic acid, and pectin.

The compositions disclosed herein or the precursors thereof may further contain porosifying agents that achieve greater surface area of, for example, an implant. Examples of porosifying agents include inorganic salts, sucrose, surfactants, small molecular weight polymers, fast degrading polymers, thermoreversible polymer precipitates, gas bubbles, and cavitation bubbles.

The amount of reversine (as well as other active ingredients, when present) in the compositions disclosed herein will depend on a number of factors and will vary from subject to subject. Such factors include the particular disorder or condition being treated, the mode of administration, the severity of the symptoms, the patient's age, weight and general condition, and the judgment of the prescribing physician.

In one embodiment, a composition comprises reversine and a pharmaceutically acceptable carrier such as a bioerodible polymer. The carrier may be used in any convenient amount relative to reversine, and the weight ratio of the carrier to reversine can vary from about 0.1 to 1 to about 100,000 to 1 depending upon the application. In one example of this embodiment, the composition consists only of reversine and a pharmaceutically acceptable carrier. In another example, the composition comprises reversine, a carrier, and one or more additional components such as those described herein. In a still further example, the composition comprises reversine, a second active agent, one or more carriers, and one or more additional components.

Methods of Use

The compositions and methods described herein are useful in the treatment of a variety of diseases and conditions. In one embodiment, a method is provided for treating a patient suffering from cancer. In another embodiment, a method is provided for prophylactically treating a patient who may be predisposed or at elevated risk for suffering from cancer. Such individuals may be identified based on a history of cancer in the individual's family, genetic screening, evaluation of the individual's risk factors including age, ethnicity, medical history, etc., and like methods. The methods of treatment involve administering a therapeutically effective amount of a composition comprising reversine to the patient. Administration of reversine may be carried out using any of the compositions, modes of administration, and dosage forms described herein.

The compositions described herein are also useful in inducing apoptosis, and are therefore useful in treating disorders responsive to the induction of apoptosis, particularly cancer. Other such disorders are well known and may be readily ascertained by one of ordinary skill in the art and/or by reference to the pertinent literature.

The compositions and methods disclosed herein may be applied to the treatment of a variety of cancers, including carcinomas, sarcomas, and cancers of the lymphatic tissue, bone marrow, and blood cells. That is, cancers characterized by the growth of solid tumors as well as cancers that are not characterized by such growth may be treated. Such cancers and related conditions include, for example, lymphoma, lymphoblastoid cells, bladder cancer, breast cancer, colon and rectal cancer, endometrial cancer, kidney (renal cell) cancer, leukemia, lung cancer, melanoma, Kaposi's sarcoma, Hodgkin's lymphoma, non-Hodgkin's lymphoma, pancreatic cancer, prostate cancer, skin cancer (melanoma and non-melanoma), uterine cancer, liver cancer, brain tumors, cervical cancer, esophageal cancer, eye cancer, stomach cancer, and thyroid cancer. One particular group of cancers that may be treated is hematological malignancies. Such cancers include leukemia, lymphoma, and myeloma. Reversine and reversine-containing compositions are useful as a primary method of treating these and other cancers, as wells as in augmenting previously-known methods of treatment such as chemotherapy and radiation therapy. In one embodiment, reversine and reversine-containing compositions are effective in treating multi-drug resistant cancers.

For example, the compositions and methods disclosed herein may be used to treat multiple myeloma (MM), including multi-drug resistant MM, as well as other types of tumor cells. A wide variety of myeloma cell lines, including primary tumor cells (see, e.g., Examples 1 and 7) have been shown to be susceptible to the anti-tumor effects of reversine. The effects of reversine include apoptosis in myeloma cells (see, e.g., Examples 5 and 8). Furthermore, in many cases, reversine has significant anti-tumor activity at concentrations as low as 1 µM or less. For a wide variety of tumor cell lines, a 0% survival rate is observed upon exposure of the cells to reversine at concentrations between 1 and 10 µM over a 72 hour period. Additional cell lines may be treated using these conditions or a variant thereof, such as treatment with higher concentrations of reversine or treatment with a composition comprising reversine and one or more additional anti-cancer active agent. In one embodiment, the reversine-containing compositions disclosed herein are effective in treating stroma-unresponsive myeloma tumors.

A desirable characteristic of any anti-tumor agent is non-toxicity toward the healthy cells that may come into contact with the agent as a result of administration of the agent. In the case of treatment of MM, such healthy cells include blood cells, bone cells and liver cells. The data provided in Examples 2 and 3 demonstrate that reversine has minimal toxicity toward stromal cells, hepatocytes, and peripheral blood mononuclear cells at concentrations as great as 10 μM or more. This data, in combination with the data provided, for example, in Examples 1 and 7, indicates that reversine has a large therapeutic index (TI).

The myeloma cell cycle typically consists of the G1, S, G2, and M phases. Orderly progression through each of these phases is vital for proper cellular reproduction. As shown in Example 5, for example, reversine is able to cause G2 arrest in myeloma cells, thereby prolonging the period during which myeloma cells remain in the G2 phase. Because of this characteristic and reversine's anti-tumor effects, reversine is ideal for methods of treatment of cancer that involve combination drug therapy. Indeed, as described supra, administration of reversine along with another anticancer drug is within the scope of this disclosure. Such additional anticancer drugs may include, but are not limited to drugs that have anti-tumor effects and target the G2 phase of the cell cycle. Combination therapy, including synergistic and additive drug combinations, are discussed in more detail infra.

Compositions comprising reversine are effective in treating cancer whether such treatment is in the presence or absence of cytokine stimulation. Cytokines are regulatory proteins that aid in generating an immune response, and cytokine stimulation increases the number of viable myeloma cells in vitro. Anti-tumor effects of reversine are observed both in the absence and in the presence of cytokines (see Example 6), thus indicating that reversine is capable of partially or completely circumventing the effects of cytokines. Indeed, anti-MM studies using a 10 μM dose of reversine show virtually no difference in the normalized data between effect of reversine treatment in the presence of cytokines and reversine in the absence of cytokines.

Without wishing to be bound by theory, it appears that the anti-cancer activity of reversine may operate through pathways previously unobserved in active anti-MM agents. Although the exact pathways and chemical targets of reversine in tumor cells are currently unknown, the data provided in Example 8 demonstrates that reversine triggers distinct molecular signaling patterns in myeloma cells compared with other anti-MM agents. For example, unlike other anti-MM agents, reversine does not cause appreciable upregulation of chaperone proteins such as Hsp70 and Hsp90. Accordingly, herein is provided a method for treating a patient suffering from cancer, including any of the cancers discussed herein (such as, for example, MM), comprising administering to the patient an effective amount of a compound that does not upregulate chaperone proteins.

Nuclear Factor kappa-B (NF-kB) is a transcription factor found in most cell types, and is involved in regulating the immune response to infection. In many cancer cells, as well as many normal cells, NF-kB is constitutively active and localized in the nucleus. It is thought that continuous nuclear Rel/NF-kB activity protects cancer cells from apoptosis and in some cases stimulates their growth. Therefore, many currently studied anti-tumor agents seek to block NF-kB activity as a means to inhibit tumor growth. As demonstrated in Example 9, however, reversine does not suppress NF-kB activity. Without wishing to be bound by theory, it appears that reversine derives anti-tumor activity through a mechanism that differs from this conventional theory of anti-tumor agents. Therefore, herein is provided a method for treating a patient suffering from cancer, including any of the cancers discussed herein (such as, for example, MM), comprising administering to the patient an effective amount of a compound that does not suppress NF-kB activity and therefore can conceivably be used for treatment of patients with tumors that become resistant to therapies which block NF-kB.

Syk is a member of the tyrosine kinase family that is mostly expressed in haematopoitic cells. The function of syk in these cells has not yet been completely established. However, as shown by the data in Example 11, cells that do not express syk are less susceptible to the anti-tumor effects of reversine as compared with cells that express syk. Without wishing to be bound by theory, reversine appears to be capable of acting as an inhibitor of kinases, including syk-related kinases (e.g. Lyn-A) which may be important for MM and for other tumors.

Without wishing to be bound by theory, it is believed that reversine interacts with A3 adenosine receptors; specifically, reversine is a selective A3 adenosine receptor antagonist. A3 receptors are present, for example, in lung tissue, liver tissue, heart tissue, kidney tissue, brain tissue, and testes tissue. Furthermore, A3 receptors play a role in inflammation, neurodegeneration, asthma, cardiac ischemia, and cancer. Because A3 adenosine receptors are generally not expressed in MM, however, the anti-MM activity of reversine does not appear to be the result of A3 adenosine receptor antagonism. Indeed, the mechanism of anti-MM activity for reversine is not well understood, and may be different from known anti-MM agents.

Reversine can be administered directly to a patient or in pharmaceutical compositions in which it is mixed with a suitable carrier, excipient and/or any of the other additives described herein. Reversine may also be administered in combination with one or more additional active agents, in which case they may be administered separately, in different dosage forms, or simultaneously, either in one dosage form or in two different dosage forms. Combination therapy is especially desirable when reversine and the additional active agent(s) exhibit synergistic effects in the patient. "Synergy" describes instances wherein the therapeutic effects of a plurality of active agents, when administered in combination, is greater than the simple summation of the therapeutic effects of the active agents when administered alone. Such synergistic effects are readily determined using known methods of testing pharmaceutical compositions such as those disclosed herein. For example, reversine shows synergistic effects when administered in combination with dexamethasone (see Example 10). Combination therapy of particular interest involves administering reversine in conjunction with conventional chemotherapy, i.e., in a dosage regimen that includes administration of an anticancer agent such as a taxane, e.g., paclitaxel, docetaxel, analogs thereof, or the like. Administering reversine with another anticancer agent may reduce the required dosage of the agent and thus reduce the many side effects of such drugs. For example, combination therapy may involve the reversine-containing compositions described herein and one or more drugs that target the G2 phase of the cell cycle.

Pharmaceutical formulations suitable for use in conjunction with the present disclosure include compositions wherein reversine (as well as any other active agents, when present) is contained in a "therapeutically effective" amount, i.e., in an amount effective to achieve its intended purpose, such as treatment of MM. Determination of a therapeutically effective amount is well within the capability of those skilled in the art. That is, for any of the present compositions, a therapeutically effective dose can be estimated initially from cell culture assays. For example, a dose can be formulated to achieve a circulating concentration range that includes an $IC_{50}$ value as determined in cell culture. Such information can be used to more accurately determine useful doses in patients.

Toxicity and therapeutic efficacy of the compositions described herein can be determined by standard pharmaceutical procedures in cell cultures or experimental animals, e.g., procedures used for determining the maximum tolerated dose (MTD), the $ED_{50}$, which is the effective dose to achieve 50% of maximal response, and the therapeutic index (TI), which is the ratio of the MTD to the $ED_{50}$. Obviously, compositions with high TIs are the most preferred compositions herein, and preferred dosage regimens are those that maintain plasma levels of the reversine and/or additional active agents from the compositions at or above a minimum concentration to maintain the desired therapeutic effect. Dosage will, of course, also depend on a number of factors, including the desired effect of the composition, the particular active agents present (when the composition comprises reversine and additional active agents), the site of intended delivery, the route of administration, and other pertinent factors known to the prescribing physician. Generally, however, dosage will be in the range of approximately 0.1 micrograms/kg/day to 100 mg/kg/day, more typically in the range of about 1.0 mg/kg/day to 10 mg/kg/day.

Administration of the compositions described herein may be carried out as part of a treatment regimen that may include multiple instances of administration of reversine-containing compositions as well as administration of other pharmaceutically active compositions. Such a regimen may be designed as a method of treatment for any of the diseases or conditions described herein, and/or as a method of long-term maintenance of the health of a patient after having been treated for any of the diseases or conditions described herein (e.g., preventing recurrences). It will be appreciated that determination of appropriate treatment regimens is within the skill of practitioners in the art. It should be noted, however, that reversine is shown herein (see Example 4, for example) to rapidly produce therapeutically desirable results in neoplastic cells. This characteristic is beneficial as it allows, in some cases, the prescribing physician to reduce the frequency with which the compositions described herein are administered. In addition, the relatively short length of time that cancerous cells must be exposed to reversine in order to produce cytotoxic effects is beneficial as it further reduces the risk of observing undesired cytotoxicity in normal cells.

Administration of the compositions described herein may be carried out using any appropriate mode of administration and dosage form. Thus, administration can be, for example, oral, ocular, parenteral, transdermal, transmucosal, sublingual, by inhalation, or via an implanted reservoir in a dosage form. The term "parenteral" as used herein is intended to include, for example, subcutaneous, intravenous, and intramuscular injection. The term "transmucosal" as used herein is intended to include, for example, rectal, vaginal, buccal, sublingual, and penile administration. The term "inhalation" as used herein is intended to include inhalation via the nose or the mouth, and includes instances wherein absorption of the composition occurs in the lungs as well as, for example, the mucosal membranes of the mouth, nose, and throat. Administration via implants is meant to include implants affixed anywhere on or positioned anywhere inside the body, including within body cavities (e.g., intraperitoneal implants, intraocular implants, implants in joints, etc.), within organs, and subcutaneously.

Depending on the intended mode of administration, the pharmaceutical composition may be a solid, semi-solid, or liquid such as, for example, a tablet, a capsule, a caplet, an aerosol, a liquid, a suspension, an emulsion, a cream, a gel, a suppository, granules, pellets, beads, a film, a powder, a sponge, or the like.

In one embodiment, the composition comprises a unit dosage form suitable for single administration of a precise dosage. In another embodiment, the composition comprises a reservoir such as in an implant capable of controlled delivery of the composition over time.

Suitable pharmaceutical compositions and dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995). A description of some, but not all, of the suitable dosage forms is provided infra.

Oral dosage forms for administration of the compositions described herein include tablets, capsules, caplets, solutions, suspensions, and syrups, and may also comprise a plurality of granules, beads, powders or pellets that may or may not be encapsulated. Preferred oral dosage forms are tablets and capsules. Oral dosage forms are suitable for compositions wherein the components (including reversine and any other active agents present) are stable and suitable for delivery via the gastrointestinal (GI) tract. Such stability and suitability is readily determined for any composition using known testing methods.

Tablets may be manufactured using standard tablet processing procedures and equipment. In addition to reversine, tablets will generally contain inactive, pharmaceutically acceptable carrier materials as described herein. Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Oral dosage forms, whether tablets, capsules, caplets, or particulates, may, if desired, be formulated so as to provide for gradual, sustained release of reversine over an extended time period. Generally, as will be appreciated by those of ordinary skill in the art, sustained release dosage forms are formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this disclosure for ocular administration include sterile aqueous solutions, suspensions, and emulsions that may be administered in the form of eye drops. Ocular dosage forms also include contact lenses impregnated with the compositions disclosed herein, wherein the contact lens allows controlled release of the composition. Ocular implants are also suitable for delivery of the pharmaceutical compositions disclosed herein, and may be implanted in any portion of the eye including the vitreous humor, aqueous humor, and sclera.

Preparations according to this disclosure for parenteral administration include sterile aqueous and nonaqueous solutions, suspensions, and emulsions. Injectable aqueous solutions contain reversine in water-soluble form. Examples of nonaqueous solvents or vehicles are described supra. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable compositions are rendered sterile by incorporation of a sterilizing agent, filtration through a bacteria-retaining filter, irradiation, or heat. They can also be manufactured using a sterile injectable medium. Any active agents present in the compositions may also be in dried, e.g., lyophilized, form that may be rehydrated with a suitable vehicle immediately prior to administration via injection.

The compositions disclosed herein may also be administered through the skin using conventional transdermal drug delivery systems, wherein reversine is contained within a laminated structure that serves as a drug delivery device to be affixed to the skin. In such a structure, the reversine composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the reversine-containing reservoir and skin contact adhesive are present as separate and distinct layers, with the adhesive underlying the reservoir which, in this case, may be either a polymeric matrix, as described above, or it may be a liquid or hydrogel reservoir, or may take some other form. Transdermal drug delivery systems may in addition contain a skin permeation enhancer.

The compositions disclosed herein may also be administered topically using conventional topical dosage forms, wherein reversine is contained within a carrier. Dosage forms suitable for topical application include, by way of example, creams, pastes, jellies, gels, ointments, liquids, foams, suspensions, and emulsions.

In addition to the formulations described previously, the compounds may also be formulated as a depot preparation for controlled release of the active agent, preferably sustained release over an extended time period. These sustained release dosage forms are generally administered by implantation (e.g., subcutaneously, intraperitoneal, intramuscularly or by intramuscular injection).

Although the compositions disclosed herein will generally be administered orally, intravenously, subcutaneously, parenterally, transdermally, or via an implanted depot, other modes of administration are suitable as well. For example, administration may be rectal or vaginal, preferably using a suppository that contains, in addition to reversine, excipients such as a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

It is to be understood that while the invention has been described in conjunction with the preferred specific embodiments thereof, the description above as well as the examples that follow are intended to illustrate and not limit the scope of the invention. Other aspects, advantages and modifications within the scope of the invention will be apparent to those skilled in the art to which the invention pertains.

EXAMPLES

General Methods and Procedures

Cell lines. ARD, ARH-77, ARK, ARO, ARP-1, BHT101, BHP-10-3, BHP-14-9, BHP-17-10, BHP-18-17, BHP-19-24, BHP2-7, BHP-5, BHP-7, DHL-4, DHL-6, DHL-7, DHL-8, DHL-10, Dox6, EJM, FRO, IM9, INA-6, JJN3, KAT-4, KAT-4B, KAT4C, KAT18, KMS-1, KMS-11, KMS-12BM, KMS-18, KMS-20, KMS-26, KMS-28-BM, KMS-28-PE, KMS-34, KMS-5, L363, LPCL-HO, LRS, MM-AS, MEG-01, MM144, MM-1R, MM-1S, MM1S-Akt, MMSV, Namalwa, NCI-H929, NOP2, NPA, OCI MY1, OCI-MY5, OCI-My7, OPM-1, OPM-2, OPM-6, RPMI8226, S6B45, SKMM2, SW579, SW1736, THLE-3, TK PCL, TT, U266, WM-WSU, WRO, XG1, and ZR-75-1 were grown in either Dulbecco's modified Eagle's medium (DMEM) (BioWhittaker, Walkersville, Md.) or Roswell Park Memorial Institute medium (RPMI) (BioWhittaker) with 100 U/ml penicillin, 100 μg/ml streptomycin and 10% fetal calf serum (FCS) (GIBCO/BRL, Gaithersburg, Md.), unless stated otherwise.

Reagents. Reversine, 2-(4-morpholinoanilino)-6-cyclohexylaminopurine was purchased from commercial sources and used at the concentrations stated in the respective example.

MTT cell survival assay. Viability of cells treated with reversine, alone or combined with other agents, was assessed by measuring 3-(4,5-dimethylthiazol-2-yl)-2,5-diphenyl tetrasodium bromide (MTT, Chemicon International, Temecula, Calif.) dye absorbance. Cells were pulsed with 1:10 the culture volume of 5 mg/ml MTT to each well for the last 4 hrs of 72 hr cultures, followed by 1.5-3 fold the culture volume of isopropanol containing 0.04N HCl. Absorbance was measured at 570/630 nm using a spectrophotometer (Molecular Devices Corp., Sunnyvale Calif.). Recombinant human IL-6 and IGF (R&D Systems; Minneapolis, Minn.) was used at 10 ng/mL and 50 ng/mL respectively, as indicated. For testing normal PBMCs, healthy donor blood was collected using heparinized tubes, separated by Ficoll (Amersham Biosciences; Sweden) gradient separation and plated at 150,000 cells per well and pre-stimulated, as indicated, with 5 ng/mL PHA (Sigma) for 24 hrs.

Activity against myeloma cells in co-culture with bone marrow stromal cells. Co-culture Stromal cells were plated at a density of 10,000 cells per well in optical 96-well plates and were incubated for 24 hrs to allow for attachment. Tumor cell lines stably expressing luciferase were plated at 1500 cells per well. Cells were treated immediately following plating and incubated for 72 hrs. Luciferin substrate was added to cultures, mixed, and incubated at room temperature. Samples were read using a Luminoskan luminometer (Labsystems, Ramsey, Minn.).

Cell death commitment assay. The minimum time length of exposure to reversine that is required to commit MM cells to apoptosis was evaluated by incubating cells in 24-well plates with reversine (1 μM) for 1, 2, 4, 8, 16 or 24 hours. At the end of this incubation, the cells were washed 3 times and incubated in drug-free medium for an additional 3 days, resulting in equal length of total incubation for all experimental conditions (40 hrs), at which point cell survival was quantified by MTT, as above, and expressed as percentage of the value obtained from respective controls.

Cell cycle analysis. Cell lines, treated with reversine for 0, 2, 4, 8,16, 24, and 48 hrs were stained using a solution of propidium iodide (Sigma) and RNase A following 70% EtOH fixation.

Immunoblotting analysis. Immunoblotting was performed by scrapping cells (1×10$^6$), centrifuged briefly and lysed for 30 min on ice in 50 mM Tris-HCl, pH 8.0, containing 120 mM NaCl and 1% Igepal, supplemented with the Complete-TM mixture of proteinase inhibitors. The samples were cleared by centrifugation (14,000 rpm, 30 min, 4° C.) and assessed for protein concentration. SDS-polyacrylamide gel electrophoresis (12%) was performed (30-50 μg of protein per lane) and the proteins were electroblotted onto PVDF membranes. After 1 hour incubation in blocking solution (5% milk in TBST), the membranes were exposed to primary antibody overnight at 4° C. Following washing in TBST, the respective secondary HRP-labeled antibody was added at 1:20,000 dilution for 1 hr at room temperature. The membrane was then washed with TBST for 45-60 min with multiple changes of the wash buffer. Following washing, the protein expression was visualized using the ECL technique. The primary antibodies used for immunoblotting were purchased from Santa Cruz Biotechnology (Santa Cruz, Calif.), Upstate Biotechnologies (Lake Placid, N.Y.) or Cell Signaling (Beverly, Mass.). Secondary antibodies were purchased from (Jackson ImmunoResearch West Grove, Pa.).

In vitro activity against kinases. Kinase activity was screened using 500 nM of reversine (in 1% DMSO) and ATP using the Invitrogen Z'-LYTE™ kinase assay platform (Invitrogen). In summary, in first reaction the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. To calculate kinase activity, the ratio of donor emission to acceptor emission after excitation of the fluorophore at 400 nm was compared.

In vitro activity against phosphatases. In vitro phosphatase activity was screened at 500 nM reversine using the DiFMUP technology (Molecular Probes). Briefly, 6,8-difluoro-4-methylumbelliferyl phosphate substrate is combined with ATP and drug. The removal of the phosphate group on 6,8-difluoro-4-methylumbelliferyl yields a more fluorescent version of the substrate than the non-hydrolyzed form. The amount of fluorescent signal directly corresponds to the level of phosphatase activity.

Anti-myeloma activity in animals. The in vivo anti-MM activity of reversine was evaluated in an established model of diffuse MM lesions in SCID/Beige mice. Briefly, male (6 to 8-week old) SCID/Beige mice, housed and monitored in the Animal Research Facility of the Dana-Farber Cancer Institute, were irradiated (300 rads) using Cs$^{137}$ gamma-irradiator source, and received (24 hrs post-irradiation) tail i.v. injections of 10$^6$ OPM2 cells suspended in total volume of 200 microL of phosphate buffered saline (PBS) per mouse. Mice were monitored for changes in body weight and signs of infection or paralysis. In accordance with institutional guidelines, mice were sacrificed by $CO_2$ inhalation in the event of paralysis or major compromise in their quality of life. All experimental procedures and protocols had been approved by the Animal Care and Use Committee of the Dana-Farber Cancer Institute. Overall survival (defined as time between i.v. injection of tumor cells and sacrifice or death) was compared in control vs. 1 mg/mg reversine-treated (P.O. twice weekly) mice by Kaplan-Meier method.

Treatment of reversine in the Side Populations of MR20 myeloma cells. MR20 cells were plated at a density of 1×10*5 cells/mL in RPMI media supplemented with Pen/Strep and 10% FBS. Reversine was added to the cells at a range of concentrations, the cells were then incubated for 72 hrs at 37 degrees C. Following the incubation period, the cells were collected and stained with Hoescht, and counter stained with 7-AAD. Reserpine, a inhibitor of the membrane transporter, was added to a sample of control cells to identify the "side population" cells (control). The samples were then analyzed on a BD FACS Aria with a UV laser to excite the Hoescht stain. The samples were first gated on the cellular fraction (by forward and side scatter), then on the viable cells (7-AAD negative), then on the Hoescht-Blue negative Hoescht-Red negative fraction representing the Side Population.

It will be appreciated that, in addition to the general methods and procedures listed supra, other routine methods and procedures that are known in the art were used in the examples that follow.

Example 1

Anti-Myeloma Effects of Reversine

Referring now to FIG. 1, reversine has anti-tumor effects in a broad range of tumor cell lines, including myeloma, leukemia, lymphoma and thyroid. Furthermore, for a subset of MM cell lines, reversine has sub-micro molar anti-tumor effect.

Example 2

Toxicity to Non-Neoplastic Cells

Figure 2:
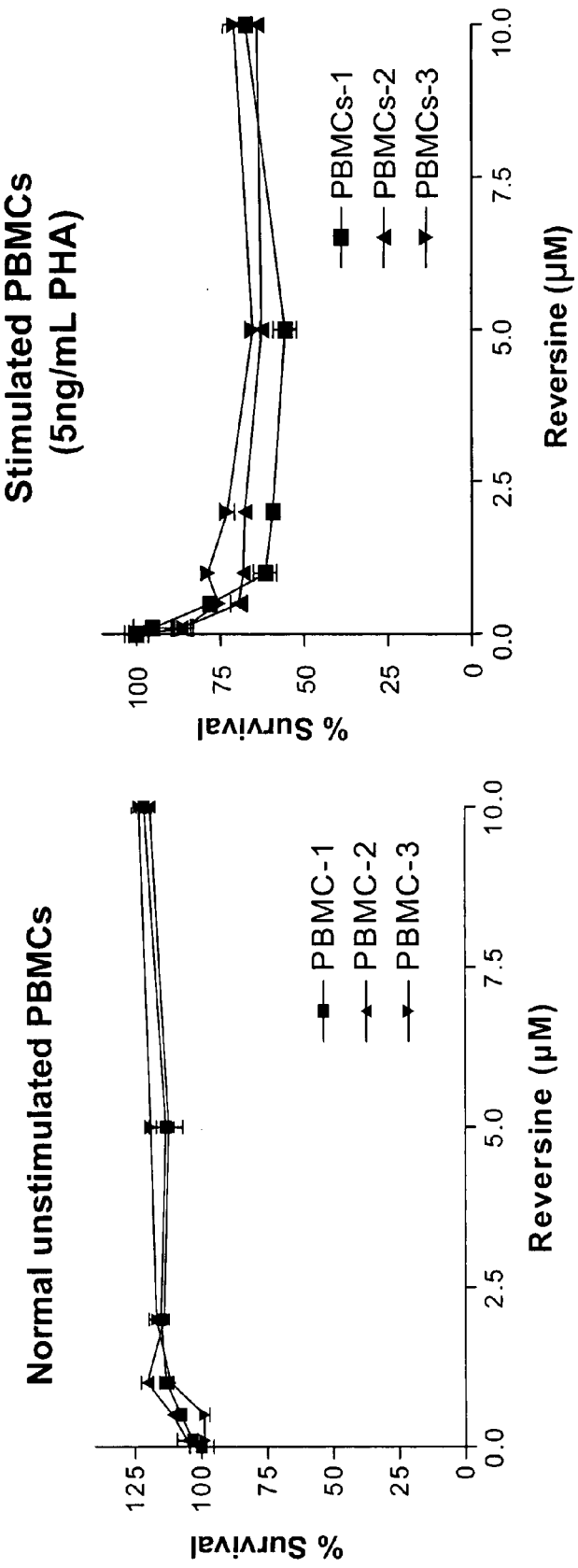
FIG. 2, described in Example 2, is a pair of graphs showing the effects of treating peripheral blood mononuclear cells (stimulated and unstimulated) with reversine.

Referring now to FIG. 2, reversine does not cause major toxicity to peripheral blood mononuclear cells (PBMCs), even at doses as high as 10 microM. Reversine also causes limited toxicity to PBMCs stimulated with phytohaemagglutinin in vitro. This data indicates a pharmaceutically acceptable window of reversine doses that have minimal toxicity to normal hematological cells.

Example 3

Toxicity to Non-Neoplastic Cells

Figure 3:
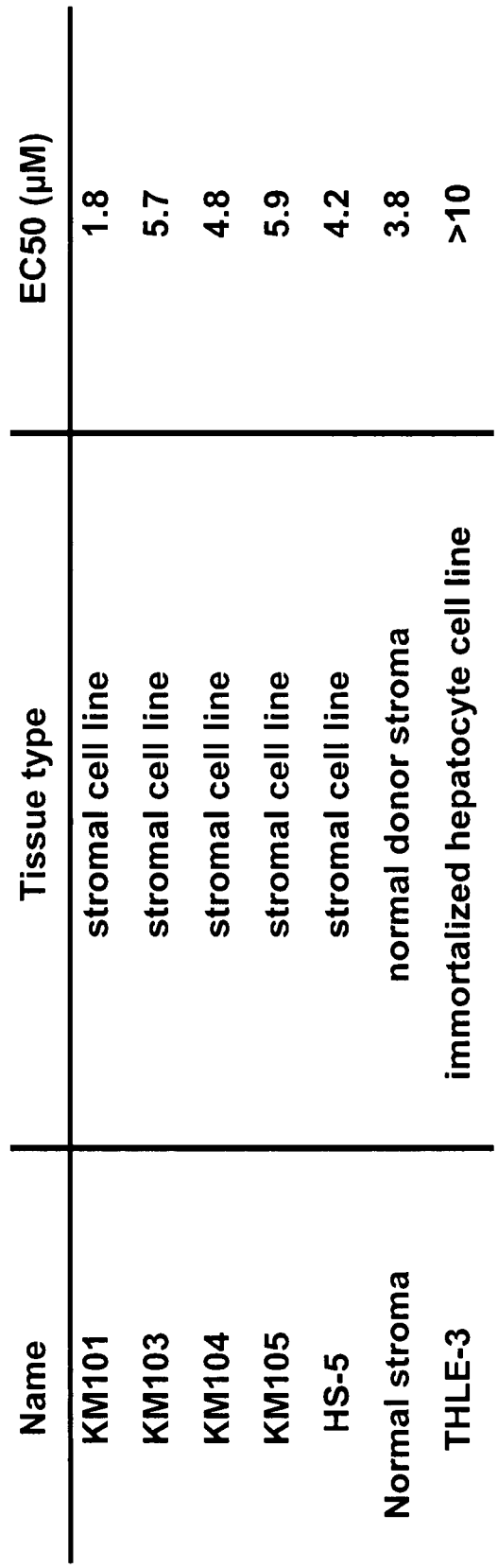
FIG. 3, described in Example 3, is a pair of graphs showing the effects of treating stromal cells and hepatocytes with reversine.

Referring now to FIGS. 1 and 3, reversine causes minimal toxicity to stromal cells and hepatocytes in vitro at 1 microM—a concentration that is toxic to a large subset of tumor cell lines, including MM cells.

Example 4

Commitment to Cell Death in Response to Reversine

Figure 4:
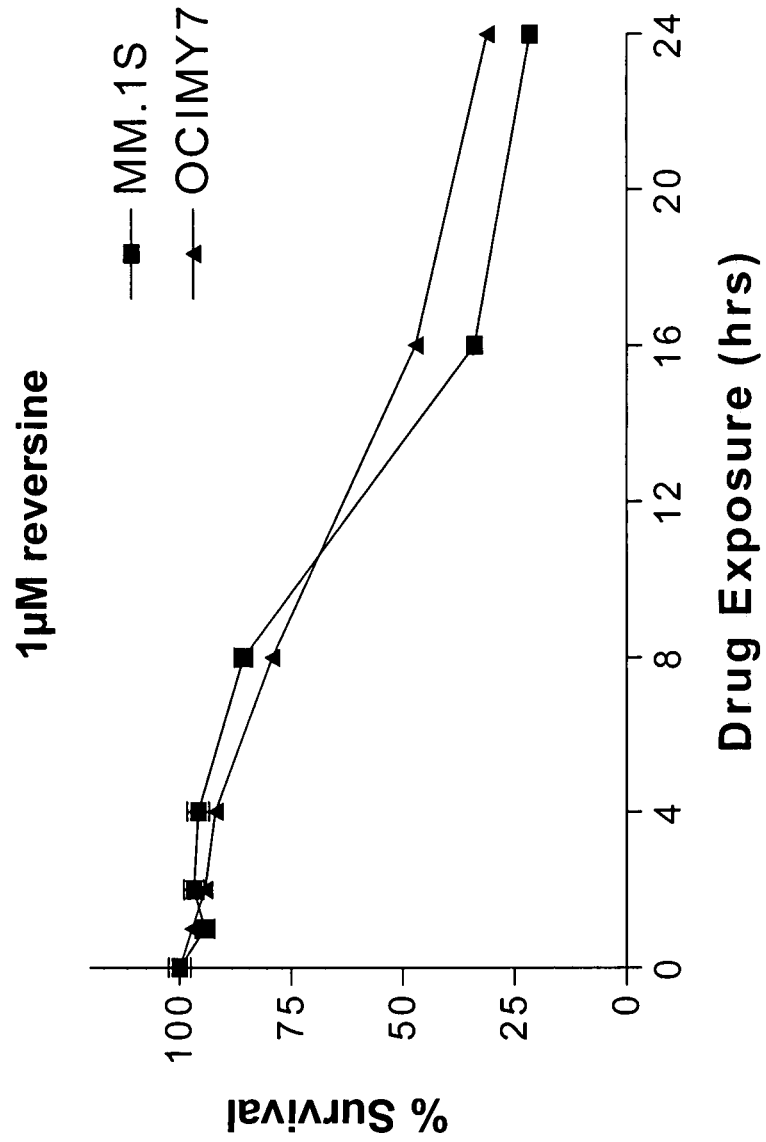
FIG. 4, described in Example 4, is a graph showing the effects of treating various tumor cell lines with reversine for periods of time lasting between 0 and 24-hours.

Referring now to FIG. 4, treatment of various MM cell lines with reversine in vitro for less than 24 hrs commits cells to death. Such activity obviates administration of reversine-containing compositions with long exposure times in vivo, thereby reducing the toxicity to normal tissues while maintaining anti-tumor activity.

Example 5

Effects of Reversine on Myeloma Cell Cycle

Figure 5:
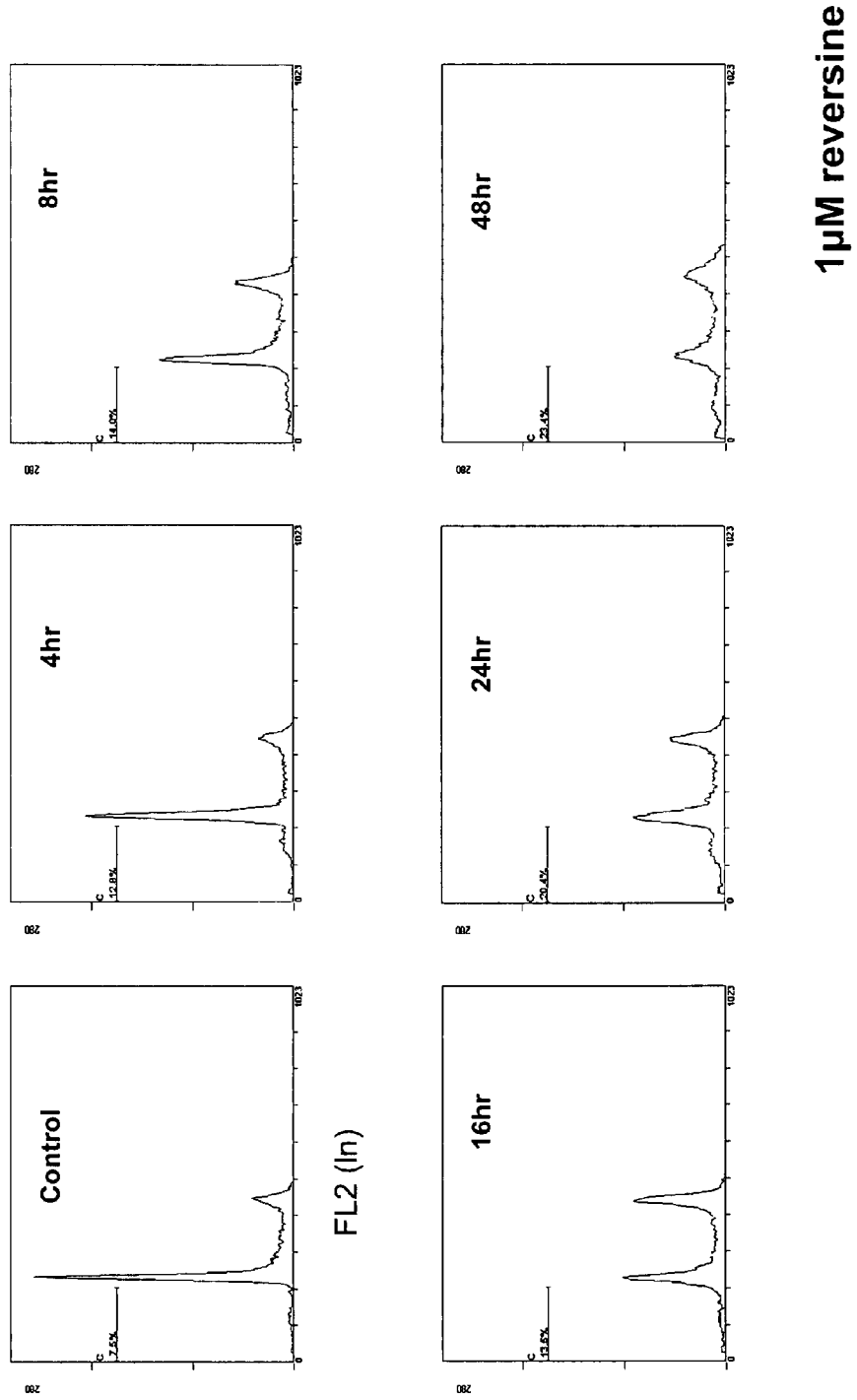
FIG. 5, described in Example 5, is a series of graphs showing the effects of a 1 micro-molar reversine solution on the cell cycle profile of MM.1S human tumor cells.
Figure 6:
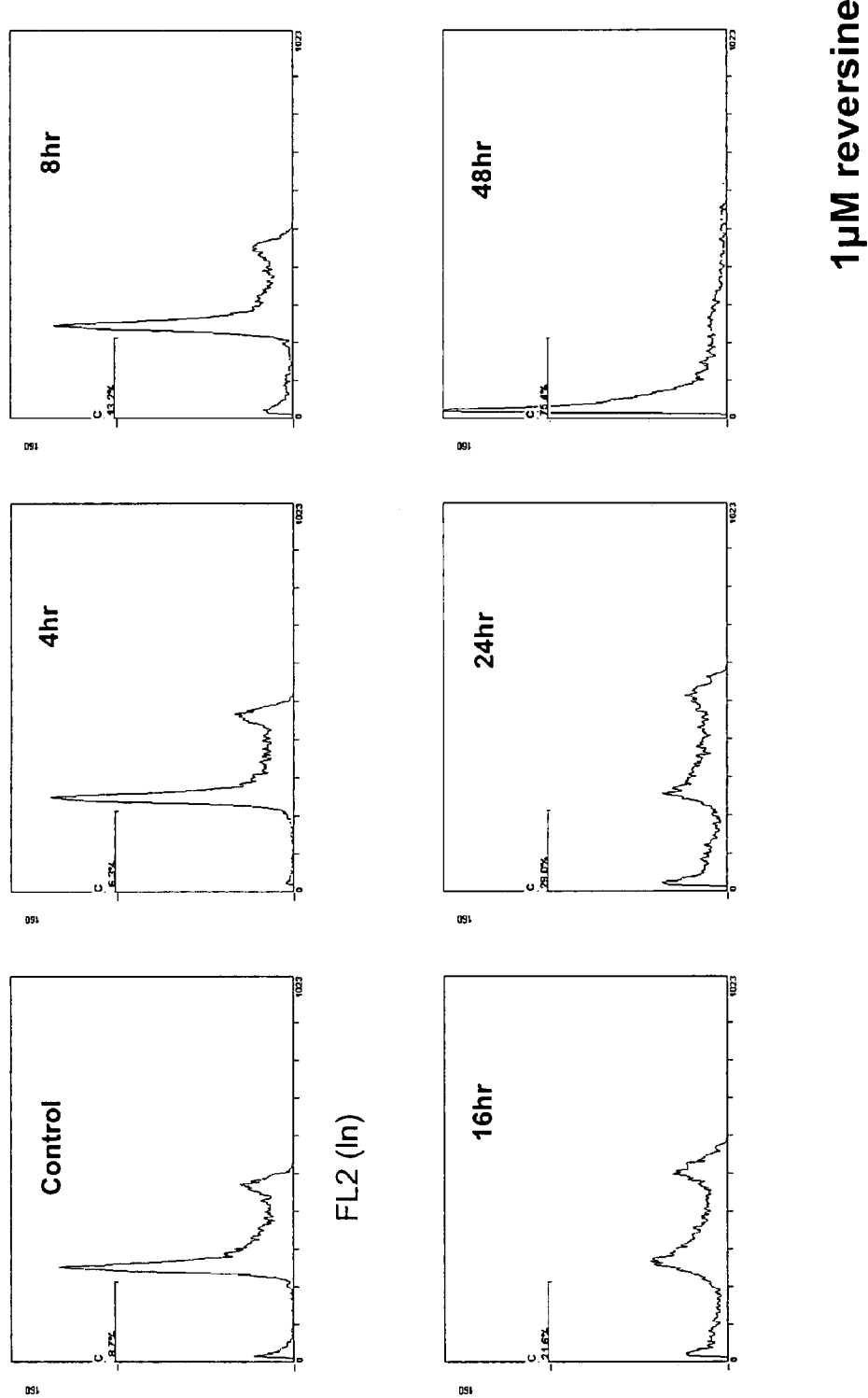
FIG. 6, described in Example 5, is a series of graphs showing the effects of a 1 micro-molar reversine solution on the cell cycle profile of OPM-1 human tumor cells.

Referring now to FIGS. 5 and 6, upon exposure of MM cells to 1 microM reversine, G2 arrest is caused 8-16 hr after initial exposure. G2 arrest is followed by an increase in the proportion of cells in the sub-G0 fraction after more than 16 hr of exposure. This indicates that cells are initially arrested in G2, followed by rapid apoptosis. Reversine is not only an inhibitor of cell proliferation, but also induces cell death in treated cells.

Example 6

Effect of Reversine in Presence or Absence of Cytokine Stimulation

Figure 7:
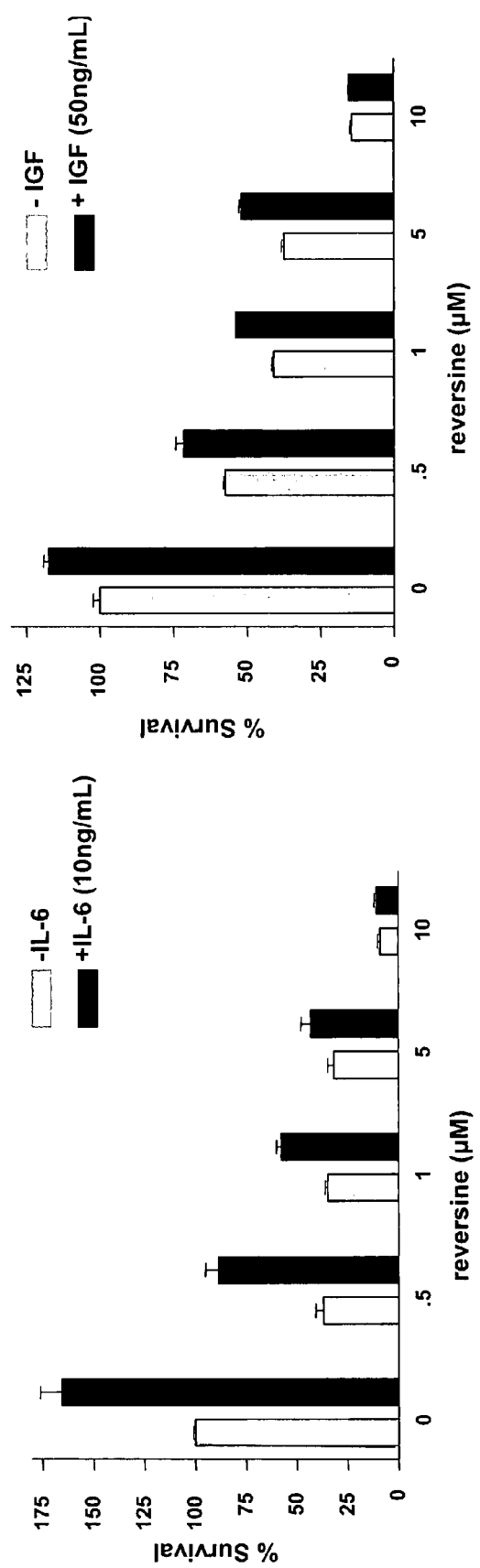
FIG. 7, described in Example 6, is a pair of graphs showing the effects of reversine on the MM-1S tumor cell line in the presence or absence of cytokine stimulation.
Figure 8:
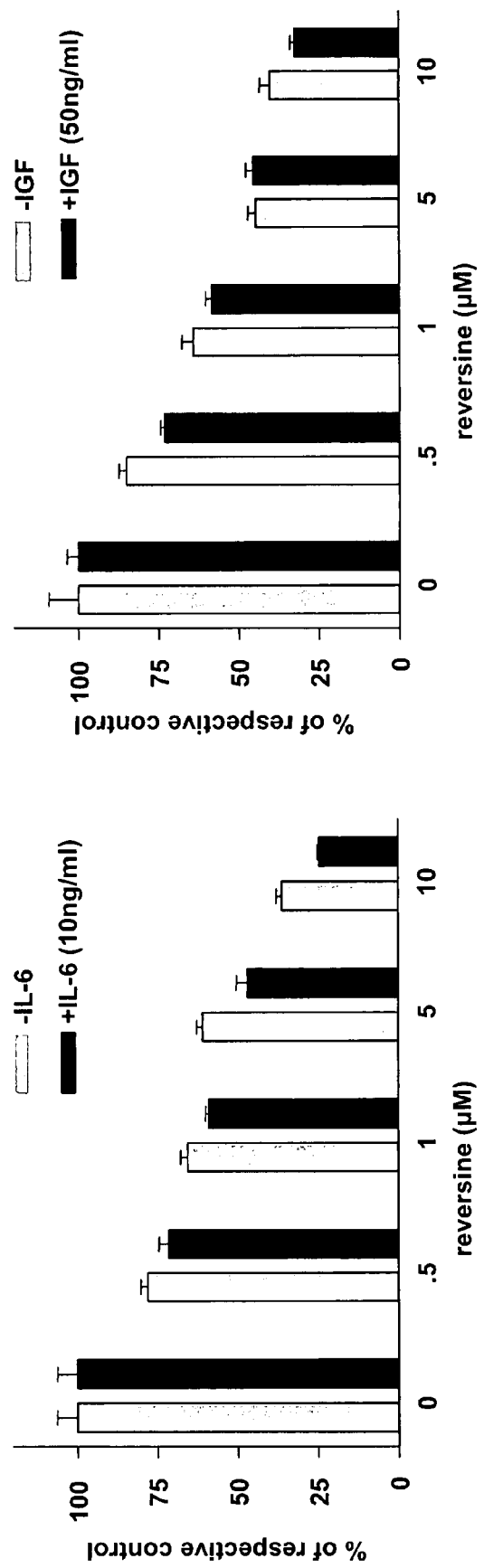
FIG. 8, described in Example 6, is a pair of graphs showing the normalized effects of reversine on the MM.1S tumor cell line in the presence or absence of cytokine stimulation. Results are presented as values normalized to the respective control.

Referring now to FIGS. 7 and 8, reversine causes a dose dependent decrease in tumor cell viability in the presence or absence of cytokines. In the absence of reversine, cytokine stimulation increases the number of viable myeloma cells in vitro. Treatment with reversine counteracts such increases. For data to each respective control, reversine is able to kill myeloma cells in the presence or absence of cytokine stimulation in a dose dependent manner.

Example 7

In Vitro Activity of Reversine Against Primary MM Samples

Figure 9:
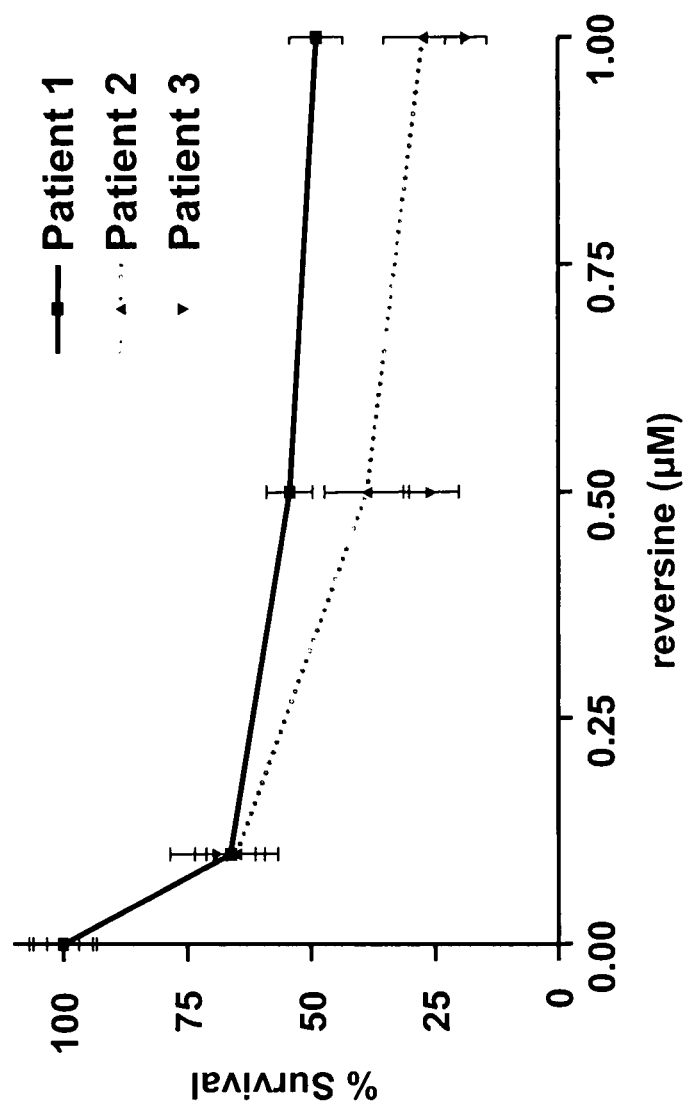
FIG. 9, described in Example 7, is a graph showing the in vitro effects of reversine against primary MM tumor cell samples.

Referring now to FIG. 9, tumor samples were collected from previously treated patients and analyzed for survival against reversine treatment. Reversine demonstrates anti-MM activity against primary myeloma tumor specimens from heavily pre-treated patients at doses ≦1 microM.

Example 8

Effects of Reversine on Signaling Cascades

Figure 10:
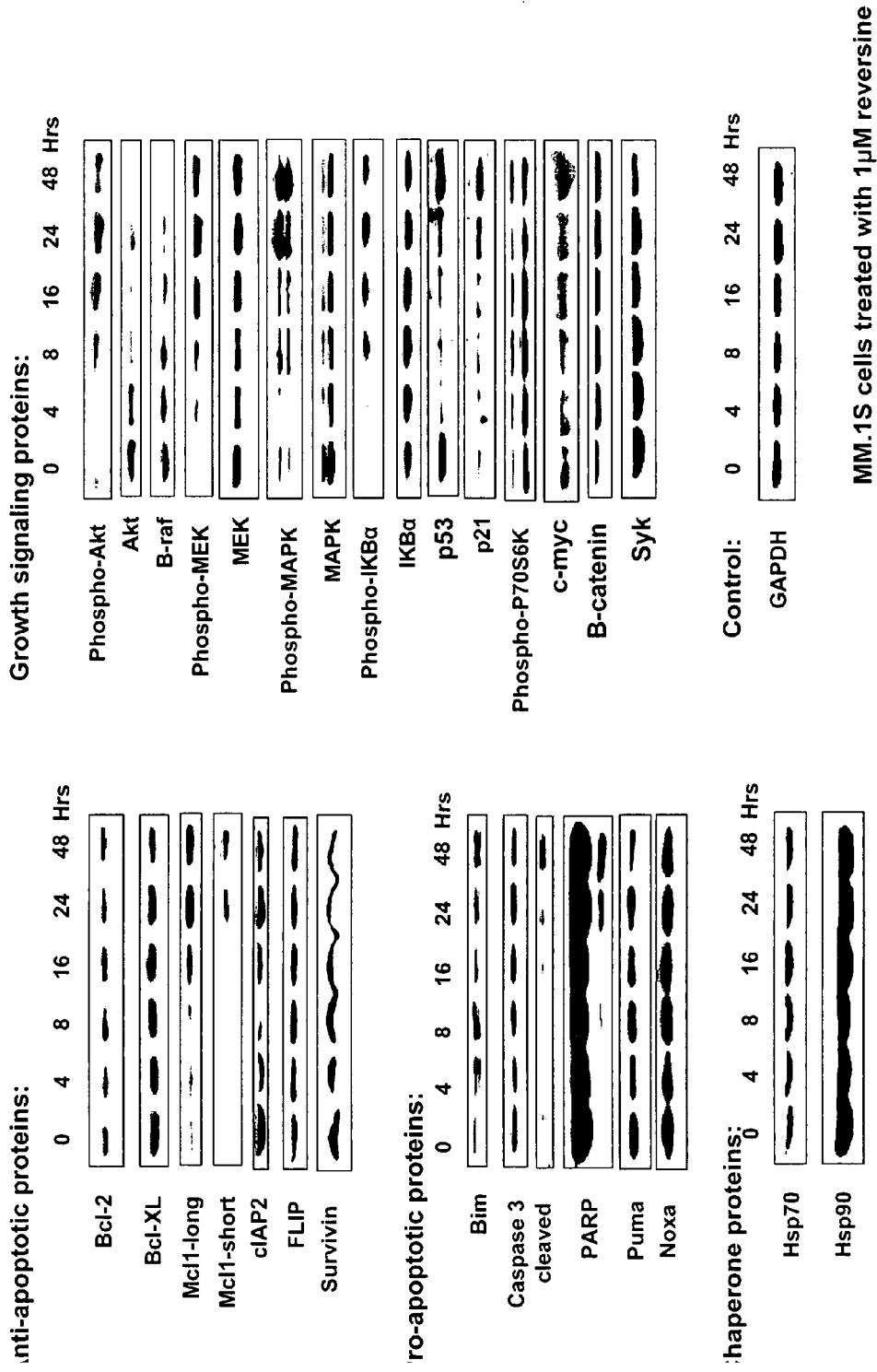
FIG. 10, described in Example 8, is a series of images showing the effects of reversine on signaling cascades of MM.1S tumor cells.

Referring now to FIG. 10, the pattern of cellular signaling responses are shown for MM.1S cells treated with 1 microM reversine for 2-48 hr. Reversine treatment causes apoptosis in myeloma cells through the cleavge of caspase 3 and PARP and also blocks growth signaling through the inhibition of B-raf and Akt levels. In contrast, to other anti-MM agents, reversine triggers distinct molecular signaling patterns in myeloma, including minimal affects on the chaperone proteins Hsp70 and Hsp90. In addition, increased levels of various phospho-specific proteins, including phospho-Akt, phospho-MEK, phospho-MAPK, phospho-IKB, and phospho-p70S6K was observed despite no increases in total protein levels. In all, treatment with reversine reveals a unique pattern of intracellular signaling from other effective anti-myeloma agents (e.g., Velcade®).

Example 9

Effects of Reversine on NF-kB Activity

Figure 11:
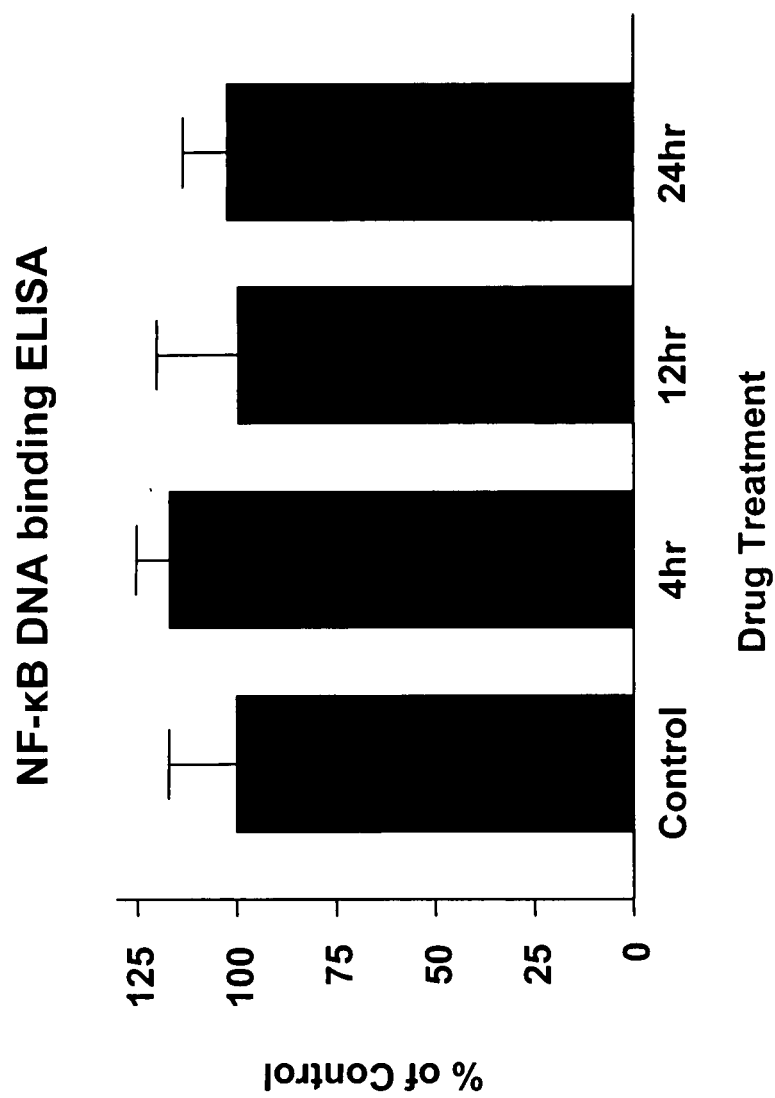
FIG. 11, described in Example 9, is a chart showing the effects of reversine on NF-kB activity.

Referring now to FIG. 11, unlike other anti-MM agents (e.g. Velcade®), reversine treatment does not suppress NK-kB binding activity, suggesting that the mechanism of action is distinct from other anti-MM drugs.

Example 10

Drug Combinations with Reversine

Figure 12:
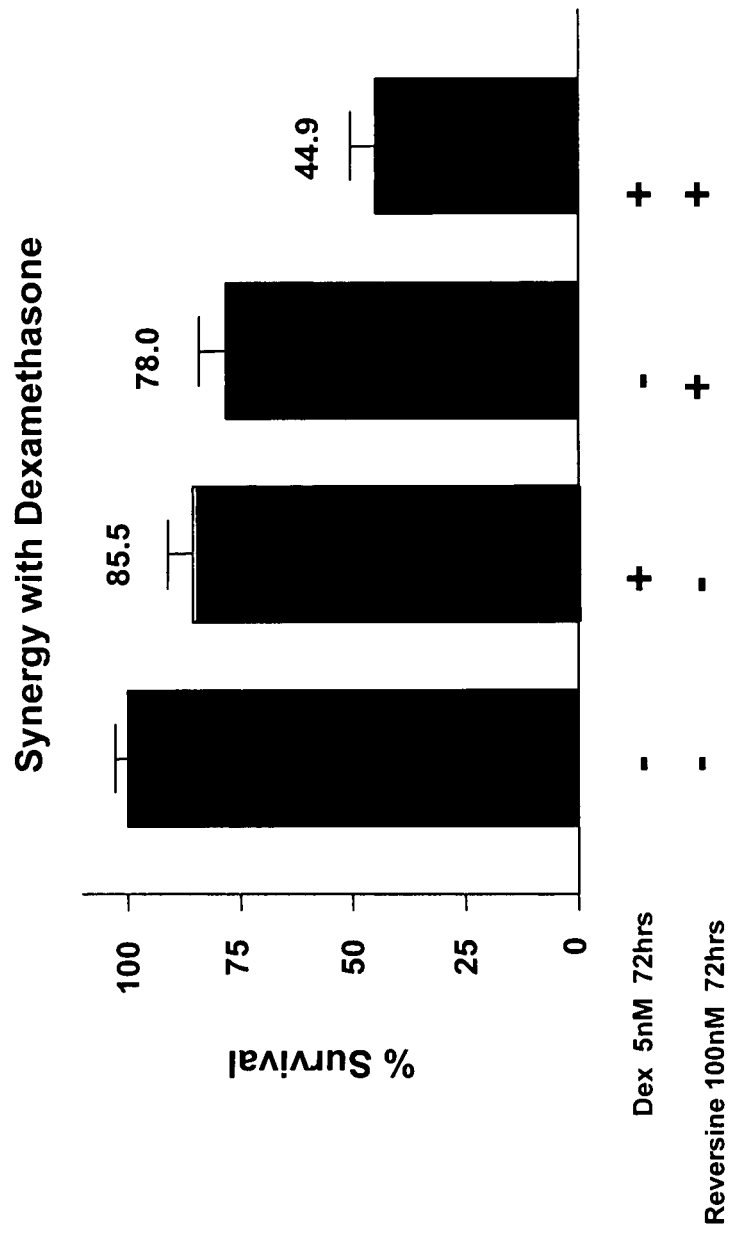
FIG. 12, described in Example 10, is a pair of charts showing the anti-MM effects of reversine in combination with other drugs.

Referring now to FIG. 12, reversine combined with low doses of dexamethasone (5 nM) results in greater than additive anti-MM activity—i.e., synergistic activity.

Example 11

Reversine Target—Syk

Figure 13:
FIG. 13, described in Example 11, is a chart comparing the effect of reversine on cells that do not express syk with the effect of reversine on cells that express syk.

Referring now to FIG. 13, in the chicken B-cell line DT40 that express syk are more sensitive to the action of reversine compared with the syk−/− version of the DT40 cells.

Example 12

Reversine Analog

Figure 14:
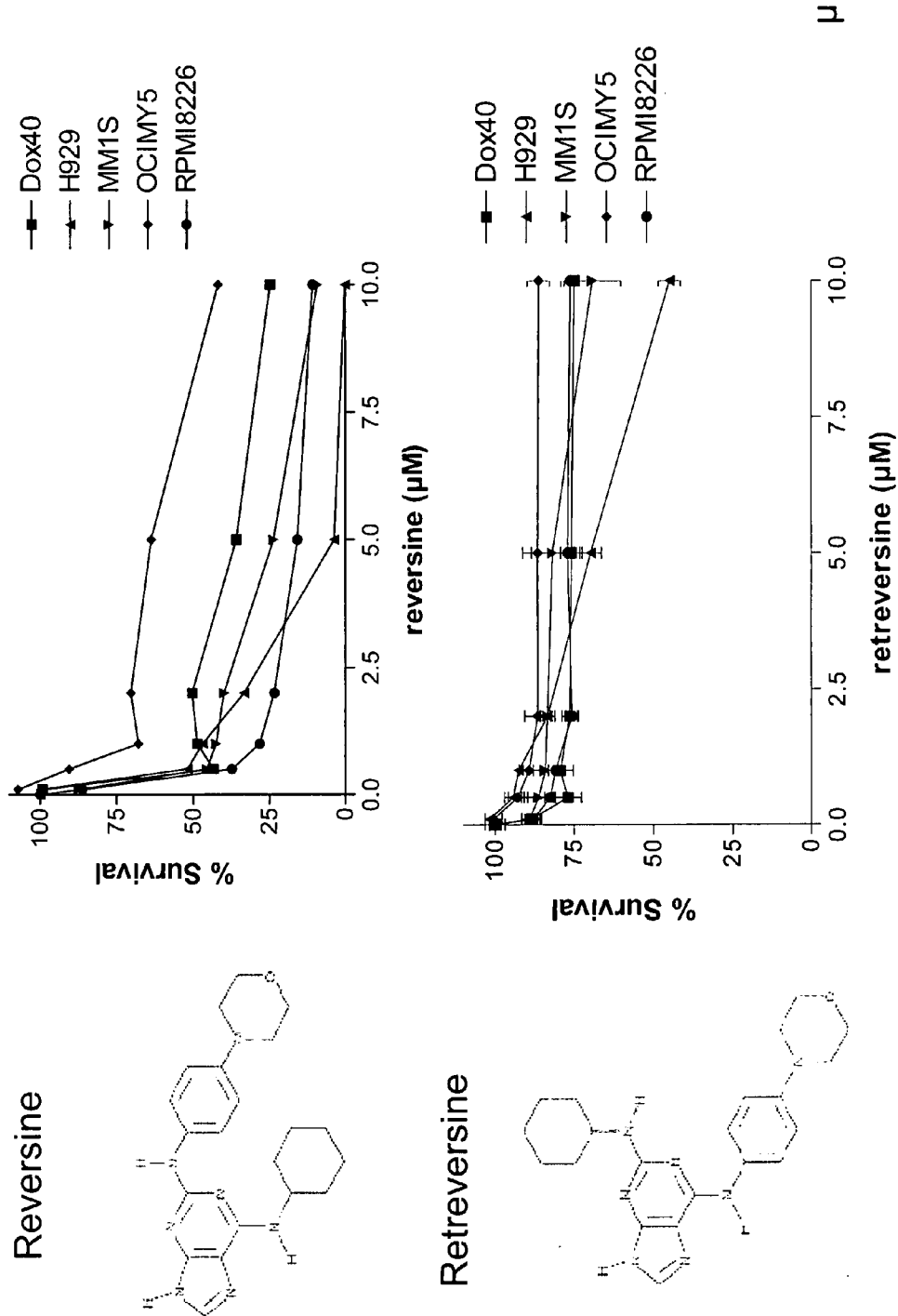
FIG. 14, described in Example 12, is a pair of graphs comparing the anti-MM activity of reversine with the anti-MM activity of retreversine.

Referring now to FIG. 14, retreversine, created by interchanging the 2 and 6-substituents on the purine ring of reversine is shown to have reduced activity in comparison with reversine.

Example 13

Reversine Kinase Inhibition

Figure 15:
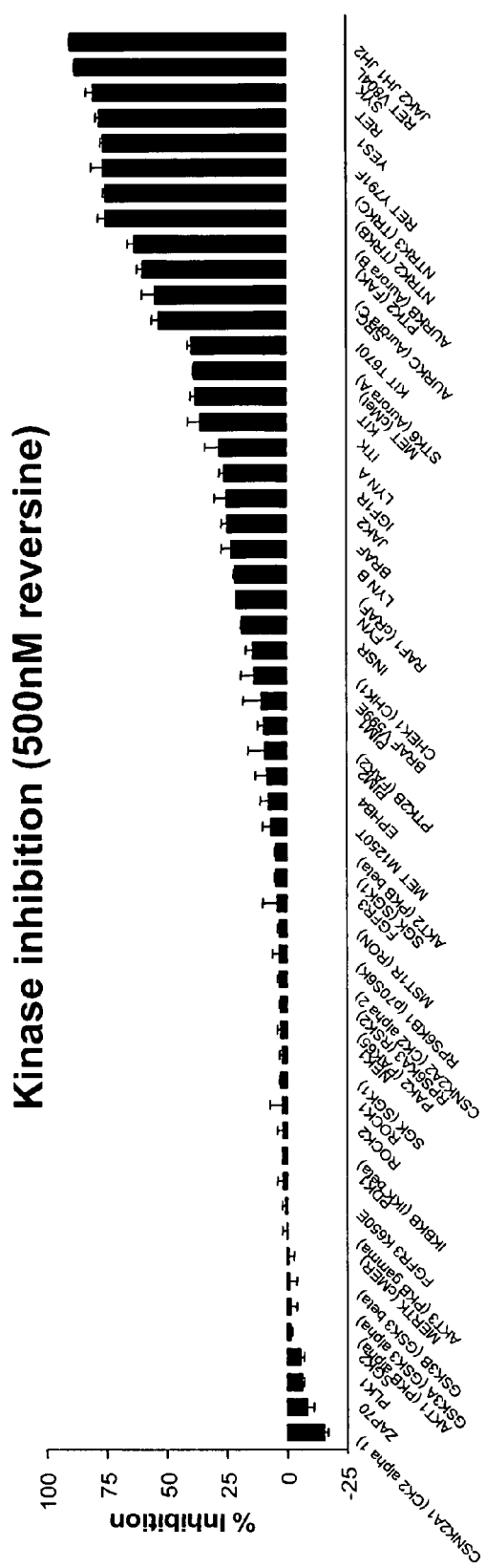
FIG. 15, described in Example 13, is a graph showing inhibition of various kinases by reversine.

Referring now to FIG. 15, inhibition of kinase activity was observed for reversine at 500 nM for various kinases.

Example 14

Reversine Phosphatase Inhibition

Figure 16:
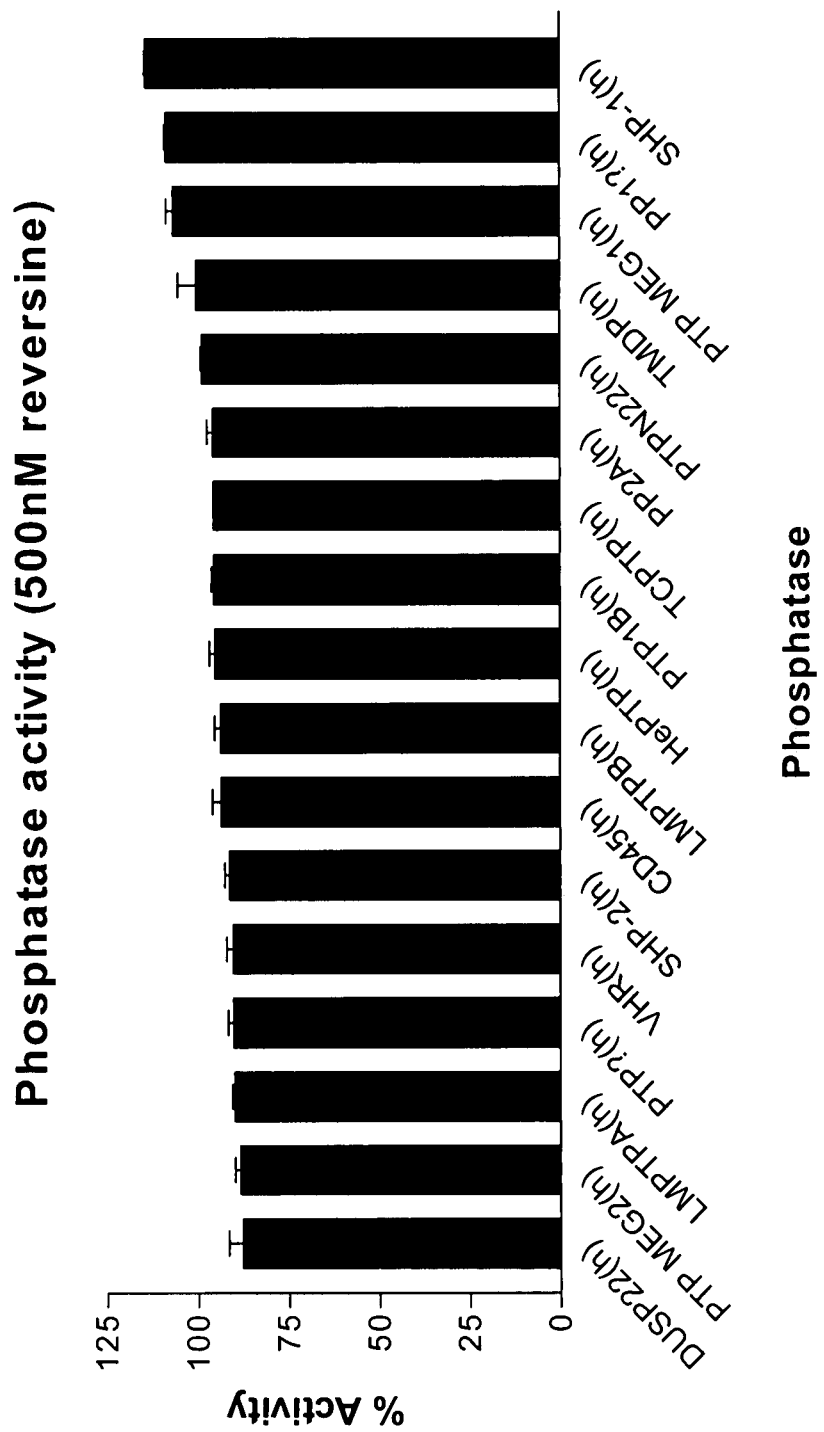
FIG. 16, described in Example 14, is a graph showing no inhibition of various phosphatases by reversine.

Referring now to FIG. 16, inhibition of phosphatase activity was not seen for reversine at 500 nM for various phosphatases.

Example 15

In Vitro Activity of Reversine in the Presence of Bone Marrow Stromal Cells

Figure 17:
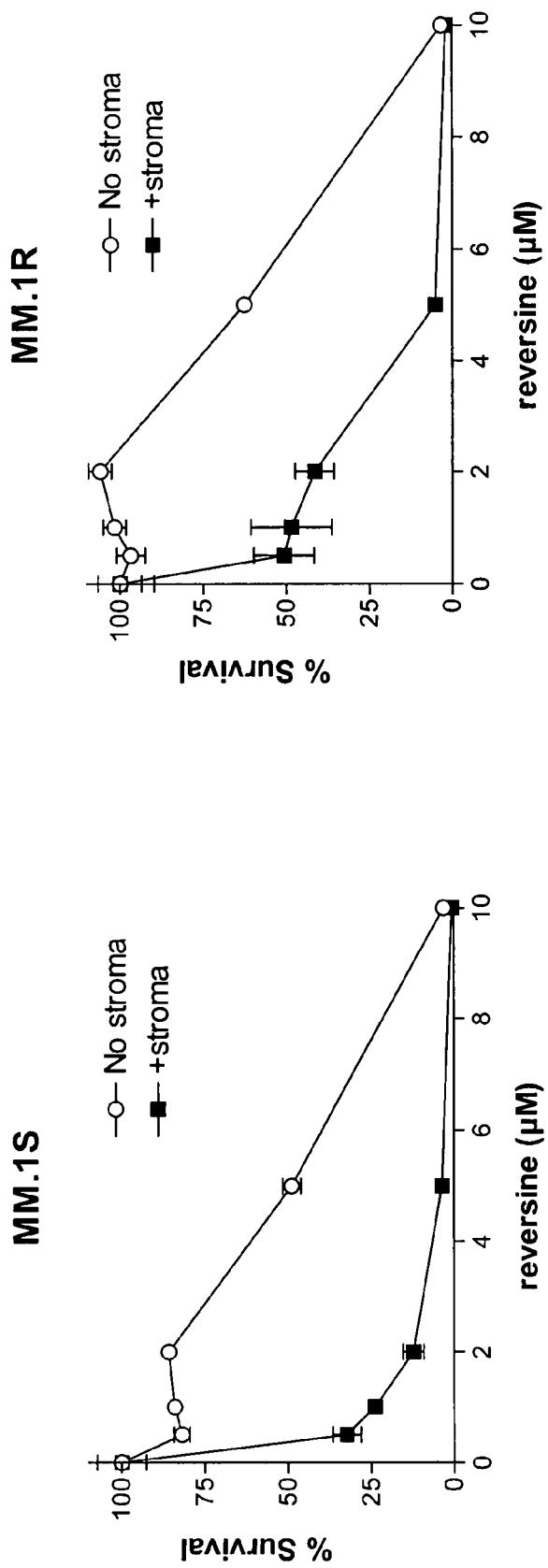
FIG. 17, described in Example 15 are line graphs showing that the sensitivity of myeloma cell lines MM.1S and MM1.R to reversine was increased when myeloma cell lines were co-cultured with bone marrow stromal cells for both GFP-luc expressing MM.1S and MM.1R cells.

Referring now to FIG. 17, sensitivity of myeloma cell lines to reversine was increased when myeloma cell lines were co-cultured with bone marrow stromal cells for both GFP-luc expressing MM.1S and MM.1R cells.

Example 16

In Vivo Activity of Reversine in a Diffuse Lesion Myeloma Model

Figure 18:
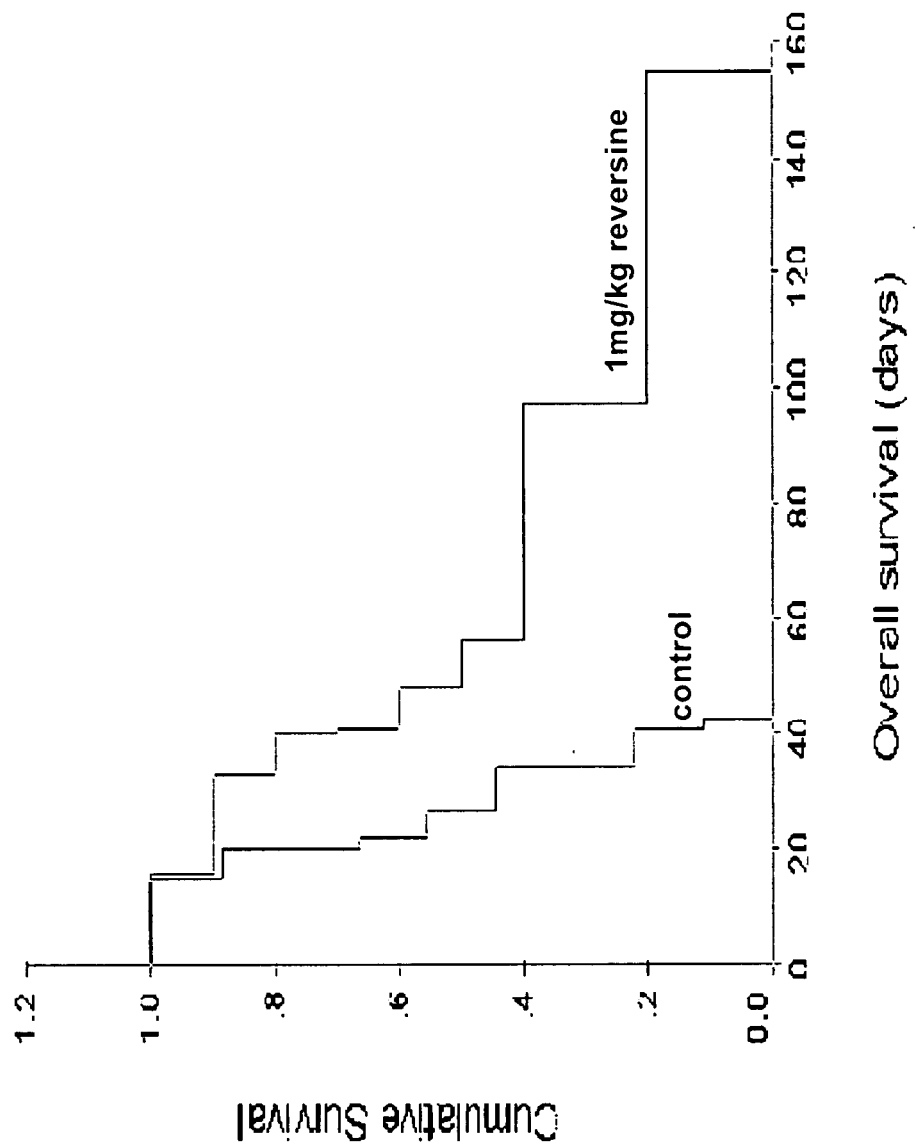
FIG. 18, described in Example 16 is graph showing extended survival of reversine treated mice compared to control mice when treated by oral gavage with 1 mg/kg reversine twice weekly following myeloma cell injection (by intravenous tail vein injection) and tumor engraftment (e.g. in the spine, skull and long bones).

Referring now to FIG. 18, activity of reversine was observed in animal experiments using mice. Survival was extended in reversine treated mice compared to control mice when treated by oral gavage with 1 mg/kg reversine twice weekly following myeloma cell injection (by intravenous tail vein injection) and tumor engraftment (e.g. in the spine, skull and long bones).

Example 17

Figure 19:
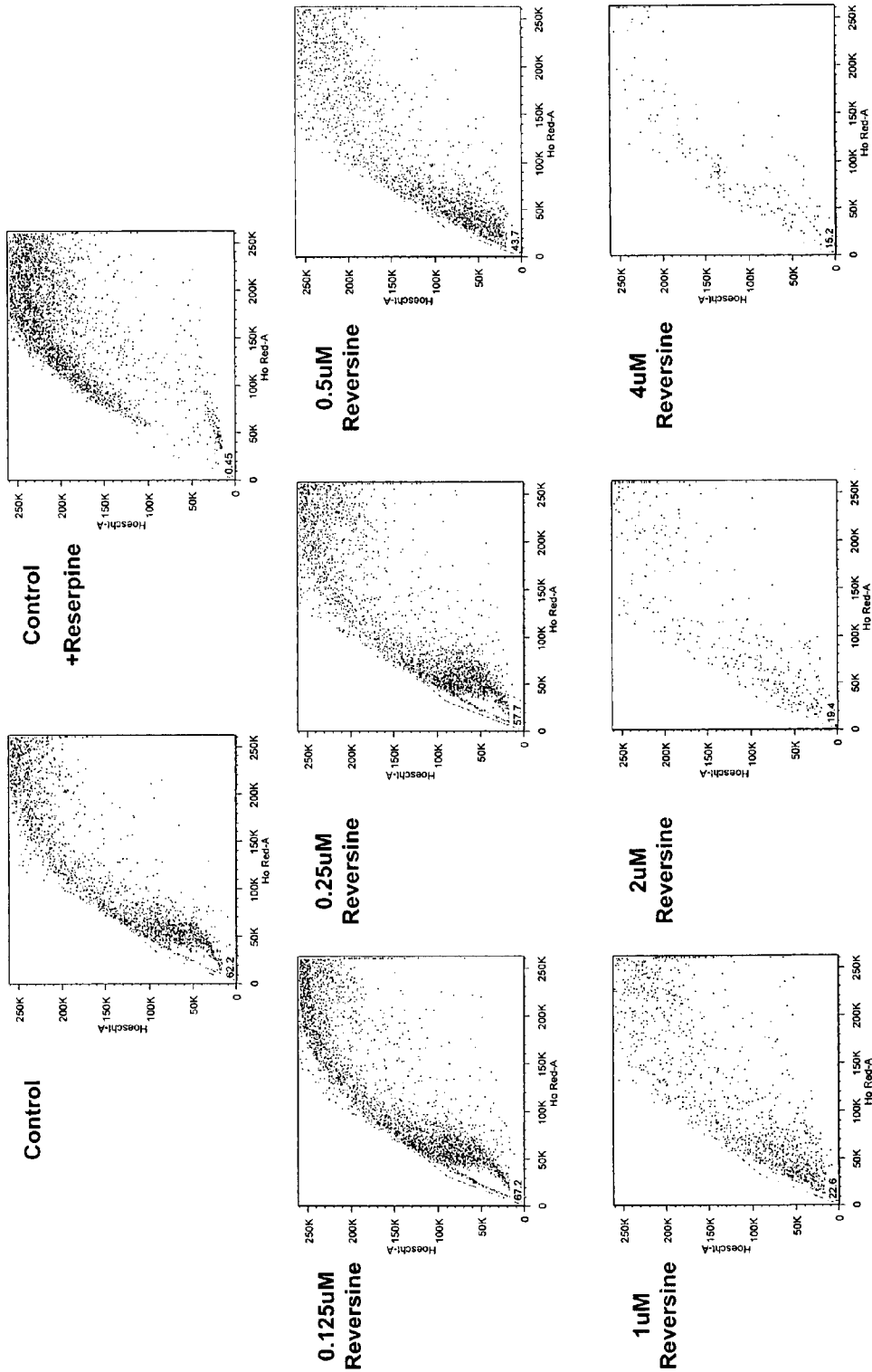
FIG. 19, described in Example 17 is a series of graphs showing the preferential effect of reversine on the side population (SP) of MR20 myeloma cells.

Preferential Effect of Reversine on the Side Population of MR20 Myeloma Cells Referring now to FIG. 19, side population (SP) cells were more sensitive than the main population to the drug. Identification of SP cells were performed using flow cytometry analysis of Hoescht stained MR20 cells following treatment with increasing concentrations of reversine for 72 hours. The percentage of SP cells decreased with increasing doses of reversine.

The invention claimed is:

1. A method for treating a hematological cancer in a patient in need thereof comprising administering to the patient a therapeutically effective amount of reversine or a pharmaceutically acceptable salt thereof.

2. The method of claim 1, wherein the hematological cancer is leukemia, lymphoma or myeloma.

3. The method of claim 2, wherein the hematological cancer is multiple-drug resistant.

4. The method of claim 1, further comprising administering to the patient a second active agent.

5. The method of claim 4, wherein the second active agent is selected from analgesic agents, anesthetic agents, anti-arrhythmic agents, antibiotics, antibodies, anti-cancer drugs, anti-cholinergics, anti-coagulative agents, anti-infective drugs, anti-inflammatory drugs, anti-nauseants, anti-Parkinson drugs, anti-proliferative agents, anti-viral agents, cytotoxic agents, immunomodulators, tumoricidal agents, and vaccines.

6. The method of claim 5, wherein the second active agent is cytotoxic, and is selected from anti-estrogens, anti-androgens, mitotic inhibitors, and anti-metabolites.

7. The method of claim 4, wherein the second active agent is selected from dexamethasone, alkylating agents, anthracyclines, thalidomide, bortezomib and other proteasome inhibitors, inhibitors of heat shock proteins, and metabolites, or salts thereof.

8. The method of claim 1, wherein the method further comprises administering to the patient one or more doses of radiation.

9. The method of claim 1, wherein the reversine is administered in a pharmaceutical composition further comprising a pharmaceutically acceptable carrier, and further wherein the pharmaceutical composition is administered in a dosage regimen.

10. The method of claim 9, wherein the dosage regimen involves administering the composition once per day.

11. The method of claim 9, wherein the dosage regimen involves administering the composition once every other day.

12. The method of claim 9, wherein the dosage regimen involves administering the composition multiple times per day.

13. The method of claim 9, wherein the composition is administered in a dosage effective to provide an amount of reversine between about 0.01 mg/kg patient and about 100 mg/kg patient.

14. A method for killing or inhibiting the growth of hematological cancer cells comprising administering to a patient in need thereof an effective amount of reversine or a pharmaceutically acceptable salt thereof.

15. The method of claim 14, wherein the reversine is administered in a composition further comprising a pharmaceutically acceptable carrier.

16. The method of claim 14, wherein the hematological cancer cells form a tumor.

17. The method of claim 14, wherein the hematological cancer cells are leukemia, lymphoma or myeloma cells.

18. The method of claim 14, wherein the amount of reversine is effective in halting or reversing the spread of hematological cancer cells in the patient.

19. The method of claim 14, wherein the amount of reversine is effective in reducing the number of hematological cancer cells in the patient.

20. The method of claim 14, wherein the amount of reversine is effective in inducing apoptosis of hematological cancer cells in the patient.

21. A method for increasing the susceptibility of myeloma cells in a patient to a tumoricidal agent by slowing or arresting the cell cycle of the myeloma cells, the method comprising administering to the patient an effective amount of reversine.

22. The method of claim 21, wherein the patient has a tumor.

23. The method of claim 22, wherein the tumor is multiple-drug resistant.

24. The method of claim 22, wherein the patient has multiple tumors.

25. The method of claim 21, wherein the cell cycle is slowed or arrested during the G2 phase.

26. The method of claim 25, further comprising administering to the patient an effective amount of a tumoricidal agent.

27. The method of claim 26, wherein the tumoricidal agent is cytotoxic to myeloma cells during the G2 phase.

28. The method of claim 26, wherein the tumoricidal agent is selected from anti-estrogens, anti-androgens, mitotic inhibitors, and anti-metabolites.

* * * * *

UNITED STATES PATENT AND TRADEMARK OFFICE
CERTIFICATE OF CORRECTION

| | | |
|---|---|---|
| PATENT NO. | : 8,466,147 B2 | Page 1 of 1 |
| APPLICATION NO. | : 12/514360 | |
| DATED | : June 18, 2013 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 936 days.

Signed and Sealed this
Twenty-third Day of December, 2014

Michelle K. Lee
*Deputy Director of the United States Patent and Trademark Office*